United States Patent
Garlow et al.

(10) Patent No.: US 10,682,103 B2
(45) Date of Patent: Jun. 16, 2020

(54) FILTER SYSTEM AND METHOD FOR IMAGING A SUBJECT

(71) Applicant: Medtronic Navigation, Inc., Louisville, CO (US)

(72) Inventors: David A. Garlow, Lynnfield, MA (US); Robert P. Cloutier, Lancaster, MA (US); Elizabeth A. Levasseur, New Boston, NH (US)

(73) Assignee: Medtronic Navigation, Inc., Louisville, CO (US)

( * ) Notice: Subject to any disclaimer, the term of this patent is extended or adjusted under 35 U.S.C. 154(b) by 239 days.

(21) Appl. No.: 15/498,921

(22) Filed: Apr. 27, 2017

(65) Prior Publication Data
US 2018/0310900 A1    Nov. 1, 2018

(51) Int. Cl.
| | |
|---|---|
| *A61B 6/00* | (2006.01) |
| *A61M 5/00* | (2006.01) |
| *A61B 6/12* | (2006.01) |
| *A61B 34/20* | (2016.01) |
| *A61B 6/06* | (2006.01) |
| *A61B 90/00* | (2016.01) |

(52) U.S. Cl.
CPC .............. *A61B 6/4035* (2013.01); *A61B 6/06* (2013.01); *A61B 6/12* (2013.01); *A61B 6/4405* (2013.01); *A61B 6/481* (2013.01); *A61B 6/482* (2013.01); *A61B 6/5205* (2013.01); *A61B 6/56* (2013.01); *A61B 34/20* (2016.02); *A61M 5/007* (2013.01); *A61B 2034/2051* (2016.02); *A61B 2034/2055* (2016.02); *A61B 2034/2059* (2016.02); *A61B 2090/3762* (2016.02)

(58) Field of Classification Search
CPC ......... A61B 6/4035; A61B 34/20; A61B 6/06; A61B 6/12; A61B 6/4405; A61B 6/481; A61B 6/482; A61B 6/5205; A61B 6/56; A61B 2034/2051; A61B 2034/2055; A61M 5/007
USPC ......................................................... 378/152
See application file for complete search history.

(56) References Cited

U.S. PATENT DOCUMENTS

| | | | |
|---|---|---|---|
| 3,048,700 A | 8/1962 | Koerner | |
| 4,896,037 A | 1/1990 | Shimura et al. | |
| 5,107,529 A | 4/1992 | Boone | |
| 5,237,599 A | 8/1993 | Gunji et al. | |
| 5,838,765 A | 11/1998 | Gershman et al. | |
| 6,215,853 B1 * | 4/2001 | Kump | A61B 6/06 378/147 |

(Continued)

FOREIGN PATENT DOCUMENTS

| | | |
|---|---|---|
| DE | 102012207626 A1 | 11/2013 |
| EP | 2591728 A1 | 5/2013 |
| JP | 2014113215 A | 6/2014 |

OTHER PUBLICATIONS

Invitation to Pay Additional Fees dated Aug. 2, 2018 in corresponding/ related International Application No. PCT/US2018/028356.

(Continued)

*Primary Examiner* — Courtney D Thomas
(74) *Attorney, Agent, or Firm* — Harness Dickey

(57) ABSTRACT

A method and system is disclosed for acquiring image data of a subject. The image data can be collected with an imaging system with at least two different energy characteristics. The image data can be reconstructed using reconstruction techniques.

21 Claims, 15 Drawing Sheets

(56) References Cited

U.S. PATENT DOCUMENTS

| | | | |
|---|---|---|---|
| 6,217,214 | B1 | 4/2001 | Cabral et al. |
| 8,238,631 | B2 | 8/2012 | Hartmann et al. |
| 2001/0001011 | A1 | 5/2001 | Salb |
| 2001/0038682 | A1 | 11/2001 | Salb |
| 2002/0037067 | A1 | 3/2002 | Horiuchi |
| 2002/0186817 | A1 | 12/2002 | Schukalski et al. |
| 2004/0264626 | A1 | 12/2004 | Besson |
| 2007/0078336 | A1 | 4/2007 | Toth |
| 2008/0279337 | A1 | 11/2008 | Yuan |
| 2010/0061519 | A1* | 3/2010 | Thomas .................. G21K 1/04 378/152 |
| 2010/0290690 | A1 | 11/2010 | Hartmann et al. |
| 2011/0075810 | A1 | 3/2011 | Sendai |
| 2012/0099768 | A1 | 4/2012 | Helm et al. |
| 2012/0099772 | A1 | 4/2012 | Helm et al. |
| 2012/0250822 | A1 | 10/2012 | Helm et al. |
| 2013/0044860 | A1* | 2/2013 | Nicholson ................ A61B 6/06 378/62 |
| 2013/0251109 | A1 | 9/2013 | Becca et al. |
| 2013/0287164 | A1 | 10/2013 | Rogers |
| 2015/0272522 | A1 | 10/2015 | Robinson et al. |
| 2015/0327821 | A1* | 11/2015 | Hu ....................... A61B 6/5205 378/62 |

OTHER PUBLICATIONS

International Search Report and Written Opinion dated Jul. 13, 2018 in corresponding/related International Application No. PCT/US2018/028362.

International Search Report and Written Opinion dated Sep. 27, 2018 in corresponding/related International Application No. PCT/US2018/028356.

International Search Report and Written Opinion dated Aug. 2, 2018 in corresponding/related International Application No. PCT/US2018/028348.

Celera Motion, Javelin™ Series Motors brochure, 5 pages, 2016.

Celera Motion, Juke™ Series Motors brochure, 2 pages, 2016.

Huestis Medical, Huestis Collimators brochure, 5 pgs., 2009.

Huestis Medical, Huestis-Cascade™ Radiographic & Fluoroscopic Radiotherapy Simulator brochure, 4 pgs., 2015.

US Digital, S4T, Miniature Optical Shaft Encoder, 5 pgs., 2015.

www.renishaw.com/en/magnetic-encoder-modules-offer-non-contact-alternative-to-potentiometers, 4 pgs., printed Apr. 11, 2017.

International Preliminary Report on Patentability dated Nov. 7, 2019 corresponding to PCT/US2018/028348.

International Preliminary Report on Patentability dated Nov. 7, 2019 corresponding to PCT/US2018/028362.

International Preliminary Report on Patentability dated Nov. 7, 2019 corresponding to PCT/US2018/028356.

* cited by examiner

FILTER SYSTEM AND METHOD FOR IMAGING A SUBJECT

CROSS-REFERENCE TO RELATED APPLICATIONS

This application includes subject matter similar to that disclosed in concurrently filed U.S. patent application Ser. No.15/498,865 and Ser. No. 15/498,964. The entire disclosures of each of the above applications are incorporated herein by reference.

FIELD

The present disclosure relates to imaging a subject, and particularly to a system to acquire image data with a duel energy imaging system.

BACKGROUND

This section provides background information related to the present disclosure which is not necessarily prior art.

A subject, such as a human patient, may select or be required to undergo a surgical procedure to correct or augment an anatomy of the subject. The augmentation of the anatomy can include various procedures, such as movement or augmentation of bone, insertion of an implant (i.e. an implantable device), or other appropriate procedures. A surgeon can perform the procedure on the subject with images of the subject that can be acquired using imaging systems such as a magnetic resonance imaging (MRI) system, computed tomography (CT) system, fluoroscopy (e.g. C-Arm imaging systems), or other appropriate imaging systems.

Images of a subject can assist a surgeon in performing a procedure including planning the procedure and performing the procedure. A surgeon may select a two dimensional image or a three dimensional image representation of the subject. The images can assist the surgeon in performing a procedure with a less invasive technique by allowing the surgeon to view the anatomy of the subject without removing the overlying tissue (including dermal and muscular tissue) when performing a procedure.

SUMMARY

This section provides a general summary of the disclosure, and is not a comprehensive disclosure of its full scope or all of its features.

According to various embodiments, a system to acquire image data of a subject, such as a living patient (e.g. a human patient), with an imaging system may use a plurality of energies. Further, enhanced contrast imaging can include a contrast agent with the plurality of energies or without. An imaging system having the plurality of energies may include a first energy source with a first energy parameters and a second energy source with a second energy parameters to energize a source. Further, the imaging system may include a plurality of sources (each source may have the same trajectory or path), wherein each source includes one or more different energy characteristics.

The imaging system can also include a pump operable to inject a contrast agent into the subject based on an instruction. A controller can be in communication with both the imaging system and the pump to provide the instruction to the pump to inject the contrast agent. The imaging system can communicate with the pump through the controller regarding timing of the injection of a contrast agent into the patient and is further operable to acquire image data based upon the timing of the injection of the contrast agent and/or the clinical procedure.

The imaging system may further include one or more filters to ensure, and/or assist in ensuring, appropriate or selected separation between the first energy characteristics and the second energy characteristics. The first energy characteristics may be selected to provide a first x-ray energy spectra with the first energy characteristics and a second x-ray energy spectra at the second energy characteristics. The filter may be provided at a selected time to assist in ensuring appropriate or selected spectra for imaging the subject, such as eliminating possible or actual overlap of the x-ray energy spectra.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 13:
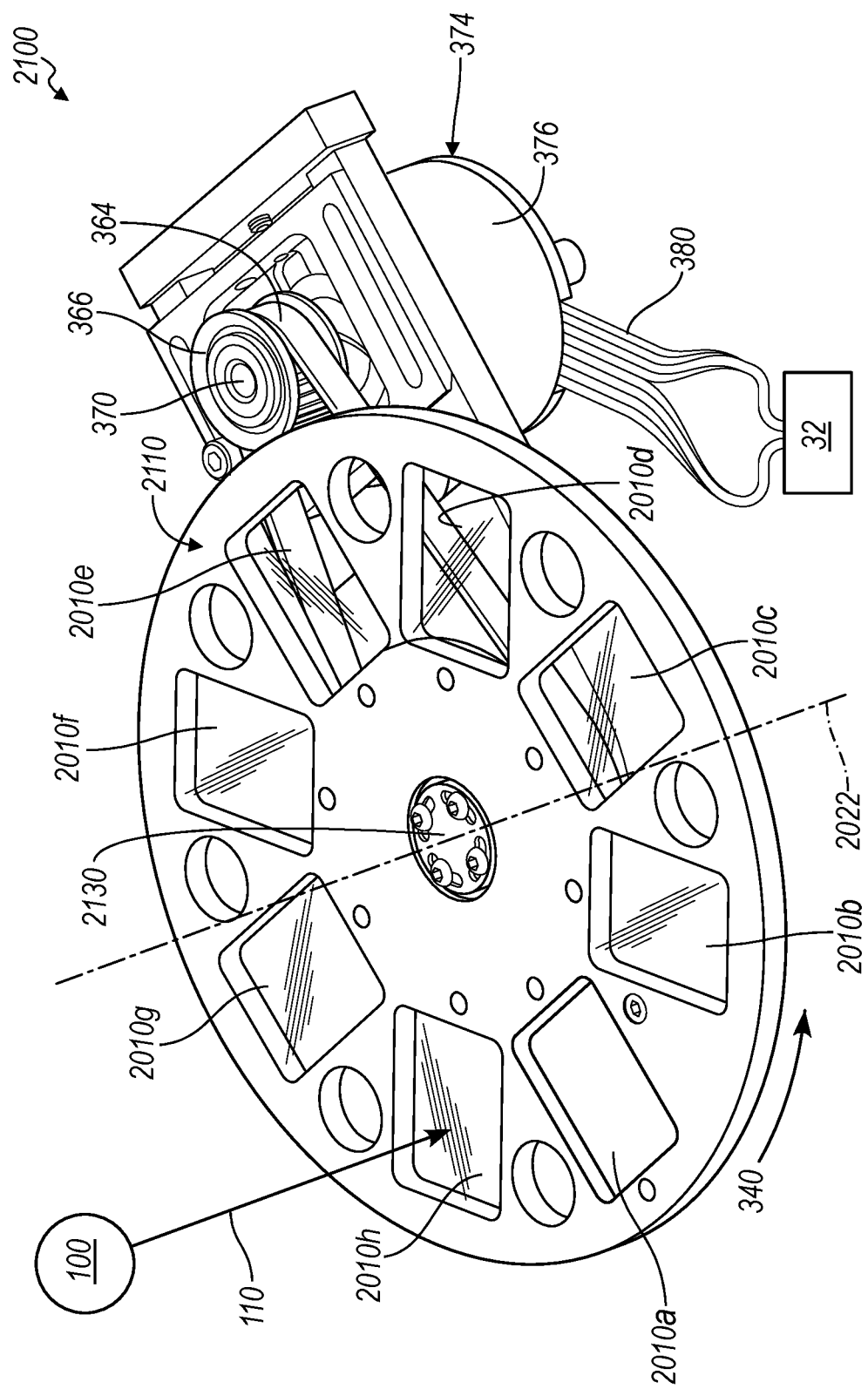
Figure 14:
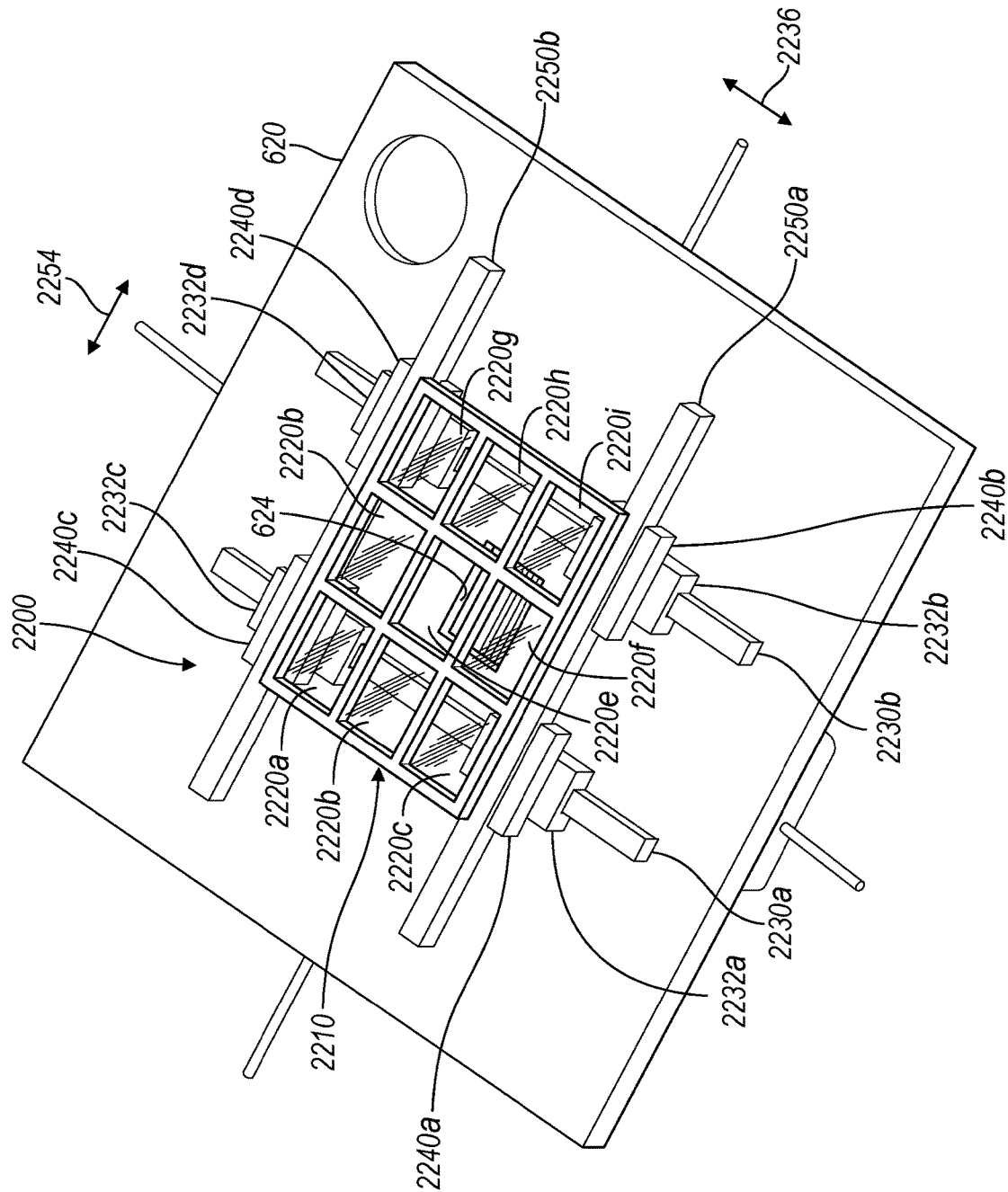

FIG. 13 a detailed view of a multiple filter filter-assembly, according to various embodiments; and FIG. 14 a detailed view of a multiple filter filter-assembly, according to various embodiments.

Corresponding reference numerals indicate corresponding parts throughout the several views of the drawings.

DETAILED DESCRIPTION

Example embodiments will now be described more fully with reference to the accompanying drawings.

Figure 1:
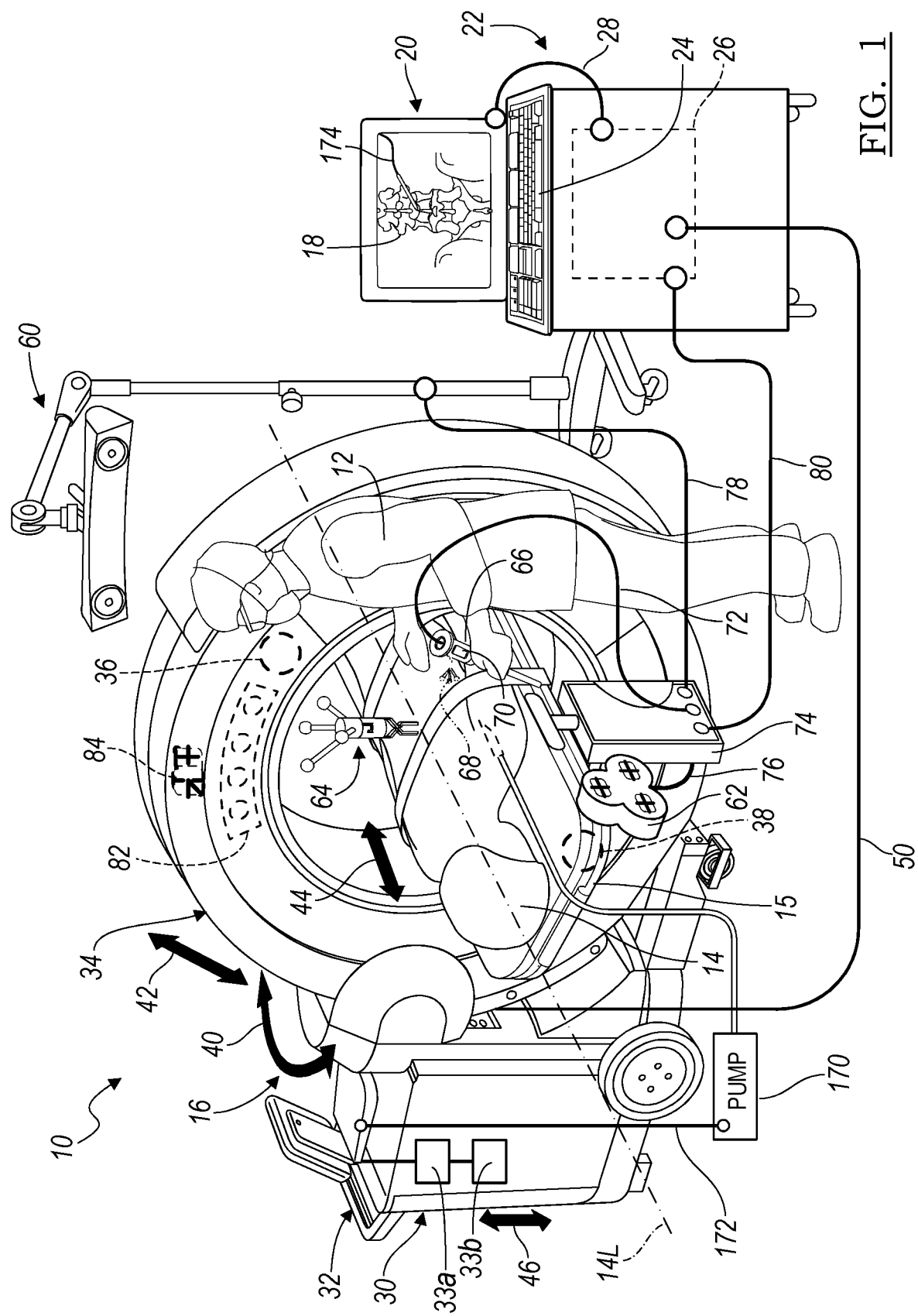
FIG. 1 is an environmental view of an imaging system in an operating theatre.

With reference to FIG. 1, in an operating theatre or operating room 10, a user, such as a surgeon 12, can perform a procedure on a subject, such as a patient, 14. In performing the procedure, the user 12 can use an imaging system 16 to acquire image data of the patient 14 to allow a selected system to generate or create images to assist in performing a procedure. A model (such as a three-dimensional (3D) image) can be generated using the image data and displayed as an image 18 on a display device 20. The display device 20 can be part of and/or connected to a processor system 22 that includes an input device 24, such as a keyboard, and a processor 26 which can include one or more processors or microprocessors incorporated with the processing system 22 along with selected types of non-transitory and/or transitory memory. A connection 28 can be provided between the processor 26 and the display device 20 for data communication to allow driving the display device 20 to display or illustrate the image 18.

The imaging system 16 can include an O-Arm® imaging system sold by Medtronic Navigation, Inc. having a place of business in Louisville, Colo., USA. The imaging system 16, including the O-Arm® imaging system, or other appropriate imaging systems may be in use during a selected procedure, such as the imaging system described in U.S. Patent App. Pubs. 2012/0250822, 2012/0099772, and 2010/0290690, all incorporated herein by reference.

The imaging system 16, when, for example, including the O-Arm® imaging system, may include a mobile cart 30 that includes a controller and/or control system 32. The control system may include a processor 33a and a memory 33b (e.g. a non-transitory memory). The memory 33b may include various instructions that are executed by the processor 33a to control the imaging system, including various portions of the imaging system 16. An imaging gantry 34 in which is positioned a source unit 36 and a detector 38 may be connected to the mobile cart 30. The gantry may be O-shaped or toroid shaped, wherein the gantry is substantially annular and includes walls that form a volume in which the source unit 36 and detector 38 may move. The mobile cart 30 can be moved from one operating theater to another and the gantry 34 can move relative to the cart 30, as discussed further herein. This allows the imaging system 16 to be mobile and moveable relative to the subject 14 thus allowing it to be used in multiple locations and with multiple procedures without requiring a capital expenditure or space dedicated to a fixed imaging system. The control system may include a processor such as a general purpose processor or a specific application processor and a memory system (e.g. a non-transitory memory such as a spinning disk or solid state non-volatile memory). For example, the memory system may include instructions to be executed by the processor to perform functions and determine results, as discussed herein.

The source unit 36 may be an x-ray emitter that can emit x-rays through the patient 14 to be detected by the detector 38. As is understood by one skilled in the art, the x-rays emitted by the source 36 can be emitted in a cone and detected by the detector 38. The source/detector unit 36/38 is generally diametrically opposed within the gantry 34. The detector 38 can move in a 360° motion around the patient 14 within the gantry 34 with the source 36 remaining generally 180° opposed (such as with a fixed inner gantry or moving system) to the detector 38. Also, the gantry 34 can move isometrically relative to the subject 14, which can be placed on a patient support or table 15, generally in the direction of arrow 40 as illustrated in FIG. 1. The gantry 34 can also tilt relative to the patient 14 illustrated by arrows 42, move longitudinally along the line 44 relative to a longitudinal axis 14L of the patient 14 and the cart 30, can move up and down generally along the line 46 relative to the cart 30 and transversely to the patient 14, to allow for positioning of the source/detector 36/38 relative to the patient 14. The imaging device 16 can be precisely controlled to move the source/detector 36/38 relative to the patient 14 to generate precise image data of the patient 14. The imaging device 16 can be connected with the processor 26 via connection 50 which can include a wired or wireless connection or physical media transfer from the imaging system 16 to the processor 26. Thus, image data collected with the imaging system 16 can be transferred to the processing system 22 for navigation, display, reconstruction, etc.

The source 36, as discussed herein, may include one or more sources of x-rays for imaging the subject 14. In various embodiments the source 36 may include a single source that may be powered by more than one power source to generate and/or emit x-rays at different energy characteristics. Further, more than one x-ray source may be the source 36 that may be powered to emit x-rays with differing energy characteristics at selected times.

According to various embodiments, the imaging system 16 can be used with an un-navigated or navigated procedure. In a navigated procedure, a localizer and/or digitizer, including either or both of an optical localizer 60 and an electromagnetic localizer 62 can be used to generate a field and/or receive and/or send a signal within a navigation domain relative to the patient 14. The navigated space or navigational domain relative to the patient 14 can be registered to the image 18. Correlation, as understood in the art, is to allow registration of a navigation space defined within the navigational domain and an image space defined by the image 18. A patient tracker or dynamic reference frame 64 can be connected to the patient 14 to allow for a dynamic registration and maintenance of registration of the patient 14 to the image 18.

The patient tracking device or dynamic registration device 64 and an instrument 66 can then be tracked relative to the patient 14 to allow for a navigated procedure. The instrument 66 can include a tracking device, such as an optical tracking device 68 and/or an electromagnetic tracking device 70 to allow for tracking of the instrument 66 with either or both of the optical localizer 60 or the electromagnetic localizer 62. The instrument 66 can include a communication line 72 with a navigation/probe interface device 74 such as the electromagnetic localizer 62 with communication line 76 and/or the optical localizer 60 with communication line 78. Using the communication lines 74, 78 respectively, the interface 74 can then communicate with the processor 26 with a communication line 80. It will be understood that any of the communication lines 28, 50, 76, 78, or 80 can be wired, wireless, physical media transmission or movement, or any other appropriate communication. Nevertheless, the appropriate communication systems can be provided with the respective localizers to allow for tracking of the instrument 66 relative to the patient 14 to allow for illustration of a tracked location of the instrument 66 relative to the image 18 for performing a procedure.

One skilled in the art will understand that the instrument 66 may be any appropriate instrument, such as a ventricular or vascular stent, spinal implant, neurological stent or stimulator, ablation device, or the like. The instrument 66 can be an interventional instrument or can include or be an implantable device. Tracking the instrument 66 allows for viewing a location (including x, y, z position and orientation) of the instrument 66 relative to the patient 14 with use of the registered image 18 without direct viewing of the instrument 66 within the patient 14.

Further, the gantry 34 can include an optical tracking device 82 or an electromagnetic tracking device 84 to be tracked with the respective optical localizer 60 or electromagnetic localizer 62. Accordingly, the imaging device 16 can be tracked relative to the patient 14 as can the instrument 66 to allow for initial registration, automatic registration, or continued registration of the patient 14 relative to the image 18. Registration and navigated procedures are discussed in the above incorporated U.S. Pat. No. 8,238,631, incorporated herein by reference. Upon registration and tracking of the instrument 66, an icon 174 may be displayed relative to, including superimposed on, the image 18.

Figure 2:
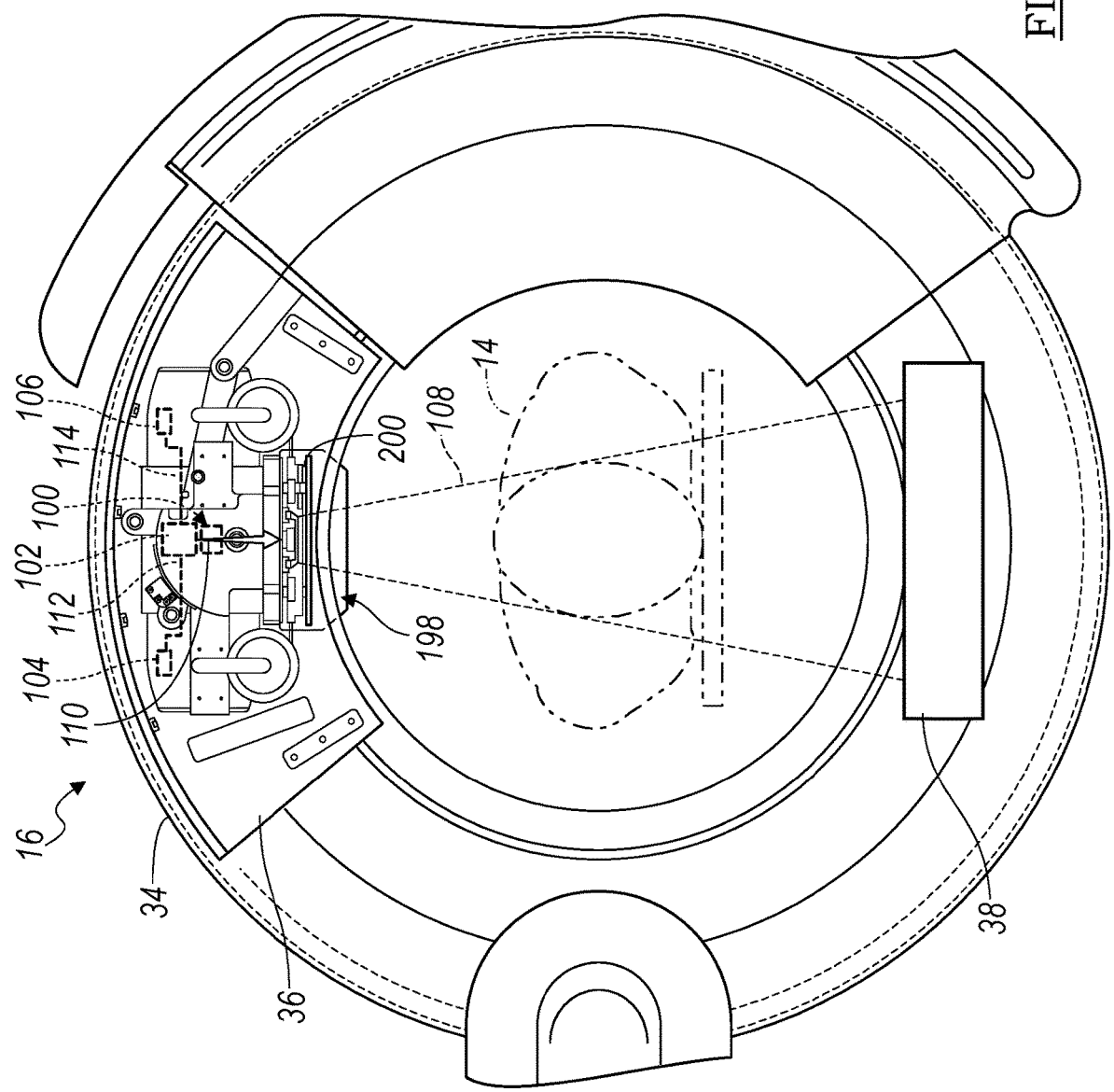
FIG. 2 is a detailed schematic view of an imaging system with a dual energy source system.

Turning reference to FIG. 2, according to various embodiments, the source 36 can include a single x-ray tube 100 that can be connected to a switch 102 that can interconnect a first power source A 104 and a second power source B 106 with the x-ray tube 100. X-rays can be emitted from the x-ray tube 100 generally in a cone shape 108 towards the detector 38 and generally in the direction from the source 100 as indicated by arrow, beam arrow, beam or vector 110. The switch 102 can switch between the power source A 104 and the power source B 106 to power the x-ray tube 100 at different voltages and/or amperages to emit x-rays at different energy characteristics generally in the direction of the vector 110 towards the detector 38. The vector 110 may be a central vector or ray within the cone 108 of x-rays. An x-ray beam may be emitted as the cone 108 or other appropriate geometry. The vector 110 may include a selected line or axis relevant for further interaction with the beam, such as with a filter member, as discussed further herein.

It will be understood, however, that the switch 102 can also be connected to a single variable power source that is able to provide power characteristics at different voltages and/or amperages rather than the switch 102 that connects to two different power sources A 104 and B 106. Also, the switch 102 can be a switch that operates to switch a single power source between different voltages and amperages. Further, the source 36 may include more than one source that is configured or operable to emit x-rays at more than one energy characteristic. The switch, or selected system, may operate to power the two or more x-rays tubes to generate x-rays at selected times.

The patient 14 can be positioned within the x-ray cone 108 to allow for acquiring image data of the patient 14 based upon the emission of x-rays in the direction of vector 110 towards the detector 38.

The two power sources A and B 104, 106 can be provided within the source housing 36 or can be separate from the source 36 and simply be connected with the switch 102 via appropriate electric connections such as a first cable or wire 112 and a second cable or wire 114. The switch 102 can switch between the power source A 104 and the power source B 106 at an appropriate rate to allow for emission of x-rays at two different energies through the patient 14 for various imaging procedures, as discussed further herein. The differing energies can be used for material separation and/or material enhanced reconstruction or imaging of the patient 14.

The switching rate of the switch 102 can include about 1 millisecond (ms) to about 1 second, further including about 10 ms to 500 ms, and further including about 50 ms. According to various embodiments, the power may be switched at a rate of about 30 Hz. Thus, x-rays may be emitted with energy characteristics according to each power source A and B for about 33 ms.

Further, the power source A 104 and the power source B 106 can be provided to include different power characteristics, including different voltages and different amperages, based upon selected contrast enhancement requirements. The different power characteristics allow the x-rays to include different energy characteristics. The differing energy characteristics of two or more different x-rays emissions interact and are attenuated (e.g. absorbed, blocked, deflected, etc.) by the same material differently. For example, as discussed further herein, different energy characteristics can be selected to allow for contrast enhancement (e.g. enhanced viewing and identification) between soft tissue (e.g. muscle or vasculature) and hard tissue (e.g. bone) in the patient 14, that may be done without any contrast agent present. Also, differing energy characteristics may assist in increasing contrast between a contrast agent injected in the patient 14 and an area without a contrast agent injected in the patient 14.

As discussed further herein, each emission of x-rays at a selected energy characteristic may include a x-ray energy spectral range. The x-ray energy spectral range for any given powering level, however, may be generally broad. Broad, for example, may include a range of energies at which x-rays are emitted and not only at a specific and/or single energy level. Thus, even if two different powering characteristics are used, emitted x-rays may overlap between two emissions of x-rays generated with the two power sources A and B. A filter assembly 200 may include a filter member of a filter material, as discussed herein, which may be used to attenuate some of the spectra of one or more of an emission of x-rays. In attenuating part of a spectrum of an emission of x-rays, differentiation between two emissions may be greater and spectral overlap may be minimized. For example, the filter member may attenuate lower energy x-rays from when the x-ray tube is powered by the higher powered power source A or B.

As an example, the power source A 104 can have a voltage of about 75 kV and can have an amperage of about 50 mA, which can differ from the power source B which can have a voltage of 150 kV and 20 mA. The selected voltages and amperages can then be switched with the switch 102 to power the x-ray tube 100 to emit the x-rays with selected energy characteristics generally in the direction of the vector 110 at and/or through the patient 14 to the detector 38. It will be understood that the range of voltages for the power source A may be about 40 kV to about 80 kV and the amperages can be about 10 mA to about 500 mA. Generally, the power characteristic differences between the first power source A 104 and the second power source B 106 can be about 40 kV to about 60 kV and about 20 mA to about 150 mA. In other words, for example, the power source B may power the x-ray tube 100 at a voltage that is about 40 kV to about 60 kV and an amperage that is about 20 mA to about 150 mA greater than power source A. In addition to the energy and mA difference, the pulse width of the exposure may be varied as well from 1 ms to 50 ms.

The dual power sources allow for dual energy x-rays to be emitted by the x-ray tube 100. As discussed above, the two or dual energy x-rays can allow for enhanced and/or dynamic contrast reconstruction of models of the subject 14 based upon the image data acquired of the patient 14. It is understood, however, that more than two power sources may be provided or they may be altered during operation to provide x-rays at more than two energy characteristics. The discussion herein of two or duel energy is merely exemplary and not intended to limit the scope of the present disclosure, unless specifically so stated.

Generally, an iterative or algebraic process can be used to reconstruct the model (such as for the image 18) of at least a portion of the patient 14 based upon the acquired image data. It is understood that the model may include a three-dimensional (3D) rendering of the imaged portion of the patient 14 based on the image data. The rendering may be formed or generated based on selected techniques, such as those discussed herein.

The power sources can power the x-ray tube 100 to generate two dimension (2D) x-ray projections of the patient 14, selected portion of the patient 14, or any area, region or volume of interest. The 2D x-ray projections can be reconstructed, as discussed herein, to generate and/or display three-dimensional (3D) volumetric models of the patient 14, selected portion of the patient 14, or any area, region or volume of interest. As discussed herein, the 2D x-ray projections can be image data acquired with the imaging system 16, while the 3D volumetric models can be generated or model image data.

For reconstructing or forming the 3D volumetric image, appropriate algebraic techniques include Expectation maximization (EM), Ordered Subsets EM (OS-EM), Simultaneous Algebraic Reconstruction Technique (SART) and Total Variation Minimization (TVM), as generally understood by those skilled in the art. The application to perform a 3D volumetric reconstruction based on the 2D projections allows for efficient and complete volumetric reconstruction. Generally, an algebraic technique can include an iterative process to perform a reconstruction of the patient 14 for display as the image 18. For example, a pure or theoretical image data projection, such as those based on or generated from an atlas or stylized model of a "theoretical" patient, can be iteratively changed until the theoretical projection images match the acquired 2D projection image data of the patient 14. Then, the stylized model can be appropriately altered as the 3D volumetric reconstruction model of the acquired 2D projection image data of the selected patient 14 and can be used in a surgical intervention, such as navigation, diagnosis, or planning. The theoretical model can be associated with theoretical image data to construct the theoretical model. In this way, the model or the image data 18 can be built based upon image data acquired of the patient 14 with the imaging device 16.

The 2D projection image data can be acquired by substantially annular or 360° orientation movement of the source/detector 36/38 around the patient 14 due to positioning of the source/detector 36/38 moving around the patient 14 in the optimal movement. An optimal movement may be a predetermined movement of the source/detector 36/38 in a circle alone or with movement of the gantry 34, as discussed above. An optimal movement may be one that allows for acquisition of enough image data to reconstruct a select quality of the image 18. This optimal movement may allow for minimizing or attempting to minimize exposure of the patient 14 and/or the user 12 to x-rays by moving the source/detector 36/38 along a path to acquire a selected amount of image data without more or substantially more x-ray exposure.

Also, due to movements of the gantry 34, the detector need never move in a pure circle, but rather can move in a spiral helix, or other rotary movement about or relative to the patient 14. Also, the path can be substantially non-symmetrical and/or non-linear based on movements of the imaging system 16, including the gantry 34 and the detector 38 together. In other words, the path need not be continuous in that the detector 38 and the gantry 34 can stop, move back the direction from which it just came (e.g. oscillate), etc. in following the optimal path. Thus, the detector 38 need never travel a full 360° around the patient 14 as the gantry 34 may tilt or otherwise move and the detector 38 may stop and move back in the direction it has already passed.

In acquiring image data at the detector 38, the dual energy x-rays generally interact with a tissue and/or a contrast agent in the patient 14 differently based upon the characteristics of the tissue or the contrast agent in the patient 14 and the energies of the two x-rays emitted by the x-ray tube 100. For example, the soft tissue of the patient 14 can absorb or scatter x-rays having an energy produced by the power source A 104 differently than the x-rays having energy produced by the power source B 106. Similarly, a contrast agent, such as iodine, can absorb or scatter the x-rays generated by the power source A 104 differently from those generated by the power source B 106. Switching between the power source A 104 and the power source B 106 can allow for determination of different types of material properties (e.g. hard or soft anatomy or between two types of soft anatomy (e.g. vessels and surrounding tissue)), contrast agent, implants (e.g. metal implants) and surrounding natural anatomy (e.g. bone), or etc. within the patient 14. By switching between the two power sources 104, 106 and knowing the time when the power source A 104 is used to generate the x-rays as opposed to the power source B 106 to generate the x-rays the information detected at the detector 38 can be used to identify or segregate the different types of anatomy or contrast agent being imaged.

A timer can be used to determine the time when the first power source A 104 is being used and when the second power source B 106 is being used. This can allow the images to be indexed and separated for generating different models of the patient 14. Also, as discussed herein, the timer, which can be a separate system or included with the imaging system 16 or the processor system 26, can be used to index image data generated with the contrast agent injected into the patient 14.

At least because the x-ray tube 100 is in a moveable imaging system, such as the imaging system 16, it can be moved relative to the patient 14. Thus, the x-ray tube 100 may move relative to the patient 14 while the energy for the x-ray tube 100 is being switched between the power source A 104 and the power source B 106. Accordingly, an image acquired with the power source A 104 may not be at the same pose or position relative to the patient 14 as the power source B 106. If the model is desired or selected to be formed of a single location in the patient 14, however, various interpolation techniques can be used to generate the model. Interpolation may between image data acquired at a first time and image data acquired at a second time. The image data at the first and second times may be generated with the two different energies. Thus, the model may be formed including image data from both energies using interpolation between the acquired image data. Further, the interpolation may be to account for an amount of movement (e.g. linear, rotational, etc.) of the x-ray tube 100 between when the projection with the power source A 104 and the projection with the power source B 106 was acquired.

The dual energy of the x-rays emitted by the x-ray tube 100 due to the two power sources 104, 106 can allow for substantially efficient and enhanced contrast discrimination determination between the vasculature and the musculature of the patient 14. Moreover, the switching by a switch 102 between the power source A 104 and the power source B 106 allows for an efficient construction of the source 36 where the single x-ray tube 100 can allow for the generation of x-rays at two different energies to allow for enhanced or dynamic contrast modeling of the patient 14, such as modeling the vasculature of the patient 14 including a contrast agent therein.

The patient 14 can also be imaged with the injected contrast agent by gating the acquisition of the image data of the patient 14 based upon the injection of the contrast agent. According to various embodiments, a contrast agent, such as iodine, can be injected into the patient 14 to provide additional contrast in the image data acquired of the patient 14 with the imaging system 16. During the image acquisition, however, the contrast agent flows through the vasculature of the patient 14 from an artery phase to a venous phase. For example, the contrast agent can be injected into the patient 14 into an artery where the contrast agent can flow through the vasculature of the patient 14 to the heart, through the heart, to the lungs through the venous system, back through the heart, and out into the arterial portion of the vasculature of the patient 14.

When acquiring image data of the patient 14 to identify or reconstruct the vasculature of the patient 14, knowing the timing of when image data is acquired relative to the timing of the injection of the contrast agent can allow for a reconstruction of the various phases based on the known movement of the contrast agent through structures of the patient 14. In other words, it is generally understood that the contrast agent will flow through the patient 14 as described above at a known or generally known rate. The dual energy x-rays, generated with the x-ray tube 100 based upon the power source A 104 and the power source B 106, can be used to generate image data of any portion of the vasculature of the patient 14.

The acquisition of the image data, therefore, can be gated relative to the injection of the contrast agent into the patient 14. For example, the controls 32 of the imaging system 16 can be associated or communicate with a control of a pump 170 (illustrated in FIG. 1) through a communication line 172 (illustrated in FIG. 1) that pumps or injects the contrast agent into the patient 14. The communication 172 between the pump 170 and the imaging device control 32 can be any appropriate communication such as a wired, wireless, or other data communication system. Also, the control for the pump 170 can be incorporated into the controls 32 of the imaging system 16 or the processor system 26.

Duel energy imaging systems may include those disclosed in U.S. Pat. App. Pub. Nos. 2012/0099768 and 2012/0097178, both incorporated herein by reference.

In addition to the generation of x-rays of different energies, including dual energy x-rays as discussed above, the filter assembly 200 can be used to assist in insuring or creating a select differentiation between x-ray spectras of x-rays of the two different energies. The filter assembly 200 can also be timed in conjunction with the pump 170 and the acquisition of the image data to assist in gating image data acquired of the patient 14. Therefore the filter assembly 200 can be operated to image the patient 14 to achieve the differentiation between the dual energies of the x-rays.

Figure 3:
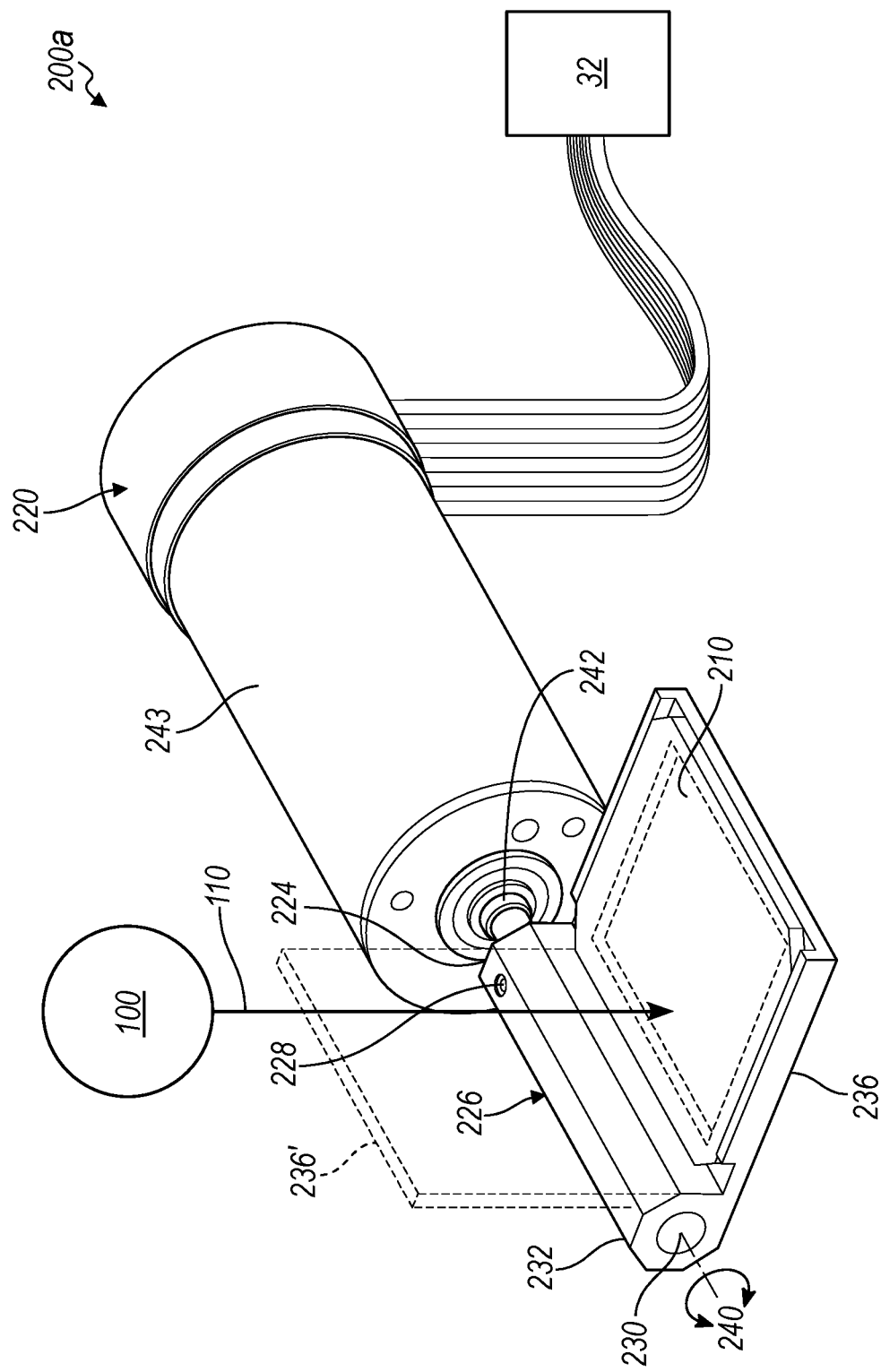
FIG. 3 is a detailed view of a filter assembly according to various embodiments.

Turning reference to FIG. 3 a filter assembly 200*a* is illustrated. The filter assembly 200*a* may be provided in the imaging system 16 such that the x-rays emitted from the x-ray tube will selectively pass through a filter member 210 of the filter assembly 200*a*. The filter assembly 200*a* may include a motor assembly 220. The motor assembly 220 may be any appropriate motor assembly that is assembled into the imaging system 16 while not interfering with operation of the imaging system 16. Exemplary motor assemblies include various stepper and/or brushless servo motors, such as the Maxon® EC-max 30 DC brushless motor sold by Maxon Motor Ag, having a place of business in Switzerland.

Generally the motor assembly 220 may be a motor assembly to rotationally drive an axle or shaft 224. Mounted to the shaft 224 may be a filter member holding member 226. The holding member 226 may be fixed to the axle 224 with a set screw in a bore 228. The shaft 224 may be received within a bore 230 of an shaft connection portion 232 of the holding assembly 226. Extending from the shaft mounting portion 232 may be a filter holding portion 236. The filter member 210 may be positioned on the holding portion 236 in a selected manner. For example, the filter portion 210 may be mounted with a fixative material, such as an adhesive, or with a mounting hardware, such as rivets or bolts. According to various embodiments the filter member 210 may be a metallic material that is brazed or welded to the holding portion 236. The holding portion may be formed as a frame, such that x-rays passing through the subject will pass only through the filter member 210 and not a portion of the holding portion 236.

The motor assembly 220 may be driven or controlled with a controller that is internal to the motor assembly 220. Further, the motor assembly 220 may be controlled with the imaging controller 32. The imaging system controller 32 may control the imaging system 16 including the filter assembly 200*a* to image the patient 14 according to a selected imaging modality. The filter assembly 200*a* may be driven or operated to assist in acquiring dual energy image data of the patient 14, as discussed further herein. The imaging sensing controller 32 may control the movement and position of the source 36 and the operation of the filter assembly 200*a*. As discussed above, the controller 32 may include a memory with a predetermined imaging protocol (including timing of imaging, number of image projections, etc.) and a related timing for operating the motor assembly 220 to move the filter.

The motor assembly 220 may include a motor assembly that is able to rotate the filter member 210 or the filter holding portion 236 substantially in either or both directions of double headed arrow 240 at a selected velocity and stopping the filter member 210 at a selected time. Generally, the motor assembly 220 may operate to move the filter member 210 in a first direction and then stop and move the filter member in a second, such as opposite, direction. For example, during operation the filter member 210 may move generally 90° into and out of the beam of x-rays, such as along vector 110. As discussed above, the x-ray beam may switch energy characteristics depending upon which power source A or B 104, 106 is powering the x-ray tube 100. The rate of switching may be about 30 Hz. Therefore, the filter member 210 may need to accelerate at about 900,000 degrees/s$^2$ to move into the beam path 110 so that the filter member 210 is appropriately positioned in about 23 milliseconds.

As schematically illustrated in FIG. 3, the x-ray tube 100 may emit to the x-rays generally in the direction of the vector 110. The x-rays will then impinge and pass through or be blocked by the filter member 210 to be filtered before reaching the patient 14 and the detector 38. When the filter 210 is selected to be filtering the x-rays from the x-ray tube 100, the filter member 210 may be moved in a first direction and positioned as illustrated in FIG. 3 such that the filter member 210 is in a first position in the path of the x-rays along ray 110. The filter member 210 may then be moved in a second direction and positioned in a second position as illustrated in phantom at 236' in FIG. 3 that is out of the x-rays path and not in the ray 110. The movement from the first position to the second position by the filter member 210 may be substantially 90° as illustrated between the carrier 236 and the carrier 236', shown in phantom.

The motor assembly 220 may, therefore, be any appropriate motor that is able to move at a selected speed. The selected speed may include time for moving the carrier 236 and emitting x-rays for acquiring image data. In various embodiments, therefore, a selected speed may include about 4500 RPM so as to move the carrier or filter holding portion 236 at a speed of about 90° about every 20 milliseconds (ms). This would allow the filter 210 to move into and out of the x-beam 110 about every 33 ms and allow about 10 ms to about 13 ms to be allocated for acquiring the image data with the x-ray beam 110. Appropriate motors may include DC servo motors, AC servo motors, stepper motors, or other appropriate motors. The motor assembly 220 may include direct drive or geared assemblies. As illustrated in FIG. 3 the shaft 224 may extend directly from the motor and engage directly in the filter holding portion 226. It is understood that the motor assembly 220, however, may also be provided to operate or move the filter holding portion 236 via a transmission or other appropriate non-direct drive system.

One or more encoders may be provided in the motor assembly 220 to determine a position of the motor including the shaft 224. For example, an encoder 242 may attach to the shaft 224 and a housing 243 of the motor assembly 220 and/or be incorporated into the motor assembly 220. The encoder 242 may include incremental or absolute encoders that may be optical, magnetic, or inductive. The encoder 242 may track or determine that the position of the shaft 224 and, therefore, the filter holding portion 226 fixedly attached to the shaft 224. For example, the encoder 242 may include a reader or a sensor at both the "in" position and "out" of beam position (illustrated in phantom 236'). The encoder 242 may then provide a signal to the controller 32 regarding the sensed location. The encoder 242 may then provide the position of the filter holding portion 226 to the image controller 32. The image controller 32 may operate the motor assembly 220 appropriately to move the filter member 210 into or out of the path 110 of the x-rays from the x-ray tube 100 based on the timing of the emission of x-rays at the selected energy and the position of the filter member 210. Thus, the movement of the filter member 210 may be timed and selected based on the timing and/or emission signal of the x-rays at the selected first or second energy.

Accordingly, during an operation the two power sources A and B 104, 106 may selectively and alternatively power the x-ray tube 100. During a selected operation, such as powering the x-ray tube with the power source B 106 the filter member 210 may be positioned in the path 110 of the x-rays in the first position. As the imaging control system 32 is able to determine and power the x-ray tube 100 with the power source B 104 the control system 32 may also operate the filter assembly 200a to move the filter member 210 into the path when powering the x-ray tube 100 with the set power source B 104. The encoder 242 may be used to determine that the filter member 210 is in the appropriate position relative to the path of the x-rays 110 to ensure the filter 210 is positioned for acquiring image data of the patient 14. When the power source A is powered to emit x-rays along ray 110, the filter member 210 may be moved by the motor assembly 220 to the second position (shown in phantom 236' in FIG. 3) out of the path of the x-rays along ray 110.

It is understood, however, that the filter holder may continuously spin on the shaft 224 in a single direction, such as in a rotation of at least 360°. The encoder 242 may then provide a signal as to when the filter member is in the in-beam position, as illustrated in solid lines in FIG. 3. The movement of the filter member 210 and the carrier 236 may then be synchronized to the emission of x-rays at a selected energy parameter with one of the selected power sources A, B 104, 106. Synchronization may occur, as discussed herein.

Moreover, it is understood that the filter carrier portion 226 may include more than one filter carrier portion 236 with more than one of the filter members 210. For example, two filter members may be provided substantially 180 degrees from each other. Such that at one speed of rotation, a filter will be in the beam path 110 twice as often. Further, any appropriate number of filter members may be provided.

As discussed above the filter material may be selected to selectively eliminate a certain portion of an x-ray spectra. As the x-rays from the x-ray tube 100 may be powered with the power source B 104 the x-rays, however, may still include a spectra that is greater than selected. Accordingly, the filter member 210 may filter the x-rays with the second energy to include a spectra that is narrower or has a higher or lower mean energy than may be provided by only powering the x-ray tube 100 with the power source B 106. Further, the filter material 210 may be selected to achieve a selected x-ray spectra, such that its average energy if approximates 60-80 kV different than its unfiltered spectrum. Accordingly, selected filter materials may include copper, aluminum, or other high-z materials. It is also understood, however, that the filter member 210 may be used to filter x-rays powered at the power source A 104. Furthermore, the filter member 210 may be used to filter x-rays powered with both power sources A and B 104, 106. And further, more than one filter member may be provided such that a first filter member will filter x-rays powered with the power source A 104 and a second filter will filter x-rays with the power source B 106.

Figure 4:
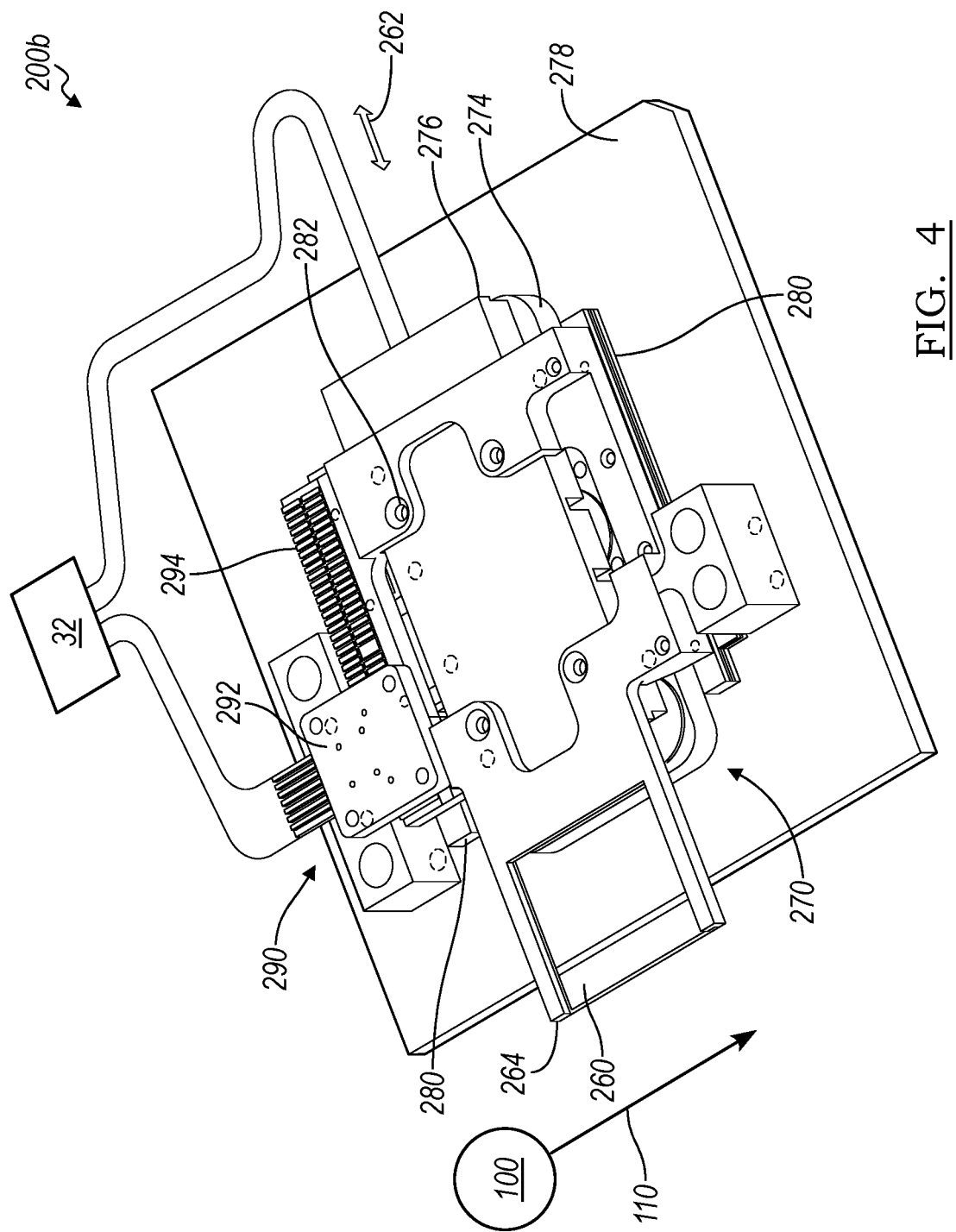
FIG. 4 is a detailed view of a filter assembly, according to various embodiments.

Turning reference to FIG. 4, a filter assembly 200b is illustrated. The filter assembly 200b may be incorporated into the imaging system 16 either with or alternative to the filter assembly 200a, discussed above. The filter assembly 200b may include a filter member or portion 260 that may be moved substantially linearly generally in two directions in a plane, such as a plane defined by the filter member 260 and/or parallel thereto, in the direction of double headed arrow 262. The filter assembly 200b may be positioned so that the filter member 260 may be moved in a first direction to a first position to intersect the beam of x-rays along vector 110 emitted from the x-ray tube 100, as schematically illustrated in FIG. 4. The filter member 260 on the filter carrier 264 may then be moved in a second, such as an opposite or different direction, to a second position such that the filter member 260 is out of the x-ray path along vector 110. The filter member 260 may be carried on a filter carrier 264 that is driven by a linear motor or actuator 270.

The linear motor 270 may include a linear motor according to various embodiments. For example, the linear motor 270 may include appropriate linear motors that include moveable or fixed magnets and moveable or fixed motor coils. Exemplary linear motors include slotless linear motors, balanced linear motors, etc. Exemplary commercially available linear motors include the Javelin™ Series Motors including models 1486 and 1487 and/or the flatbody Juke™ Series Motors sold by Celera Motion having a place of business in Loomis, Calif. The linear motor 270 may move the filter carrier 264 in the plane relative to the ray 110 of the x-rays at a selected rate and/or at a selected time. As discussed above, x-rays at the different energy characteristics may be emitted from the x-ray tube 100 at a frequency of about 30 Hz. Therefore the filter member 260 generally would need to move into the ray 110 within about 23 milliseconds to allow for an exposure of about 10 milliseconds of the patient 14 to the x-ray. Thus, the filter member 260 may be timed to move into and out of the x-ray beam to affect only the selected beam of x-rays at a selected energy characteristic, such as to have the effect of eliminating a portion of the emitted x-ray spectra.

According to various embodiments, the linear motor 270 may include a stationary linear motor coil 274 and a moving magnet 276. The stationary coil 274 may be fixed to a structure, such as a base plate or member 278 and/or one or more linear bearings 280. The moving magnet 276 positioned over the or relative to the stationary linear motor coil 274 may move generally in the direction of the double headed arrow 262. The filter carrier 264 may be mounted to the moving magnet 276 using an appropriate mechanism, such as an adhesive, screws, rivets, or the like. For example, one or more bores 282 may be provide in the filter carrier 264 to allow for a fixation member, such as a screw, to fix the filter carrier 264 to the moving magnet 276.

In operation, the moving magnet 276 may be driven in the directions of arrow 262 by the stationary motor coil 274. The operation of the linear motor in such a configuration is generally understood by one skilled in the art, and will not be described herein in detail. Nevertheless, the stationary motor coil 274 may be operated to sequentially power coils within the stationary motor coil 274 to move the moveable magnet 276 via magnetic field interactions with the moveable magnet 276. The moveable magnet 276 may include permanent and/or electromagnets that interact with coils in the stationary coil 274 to move the moveable magnet 276. As the filter carrier 264 is fixed to moveable magnet 276, the filter carrier 264 carrying the filter 260 may move with the moveable magnet 276. The linear bearings 280 may hold and guide the filter carrier 264 connected to the moveable magnet 276 in a selected manner. The linear bearings 280 may ensure that the filter carrier 264 and the moveable magnet 276 move generally in the direction of arrow 262.

The driving motor coil 274 may be connected to the image controller 32 to operate the motor 270 according to a predetermined timing or gating of positioning the filter 260 in the x-rays. As discussed above in relation to the filter assembly 200a, the image controller 32 controls and determines the timing of imaging with the x-rays. The image controller 32 includes a predetermined timing for powering x-rays at selected energies to acquire image data of the patient 14. Therefore, the image controller 32 may control the linear motor 270 to move the filter member 260 into and out of the vector 110 of x-rays from the x-ray tube 100 according to a determined or predetermined x-ray imaging plan. As discussed above, the controller 32 may include a memory with a predetermined imaging protocol (including timing of imaging, number of image projections, etc.) and a related timing for operating the motor assembly 270 to move the filter.

For example, the imaging controller 32 may include a selecting time and/or frequency of emitting x-rays powered by either or both of the power source A 104 and the power source B 106. The movement of the filter member 260 into the x-ray beam along vector 110 may be selected and timed relative to the emission of x-rays. The movement of the filter member 260 with the linear motor 270 may be synchronized to the emission of the x-rays. In various embodiments, the movement of the filter 260 with the linear motor 270 controlled by the controller 32 may be cyclic according to a predetermined cycle or may be infrequent according to a selected imaging protocol. Nevertheless, the controller 32 may control the motor 270 to move the filter member 260 in the direction of the double headed arrow 262 to position the filter member 260 in the ray 110 of the x-rays or to move it out of the way.

The position of the motor 270 may be determined with an encoder, such as a linear encoder 290. The linear encoder 290 may include an inductive encoder having a fixed read head 292 and a rail 294 connected to and moveable with the filter carrier 264. It is understood, however, that this may be vice-versa so that the read head 292 moves with the moveable with the filter carrier 264 while the rail 294 is fixed relative thereto. Nevertheless, the read head 292 may also be connected to the controller 32 so that the read head 292 is operable to transmit a signal (e.g. a position signal) to the controller 32 regarding a position of the filter carrier 264. Based on the signal, the controller 32 may determine an absolute or an incremental position of the filter carrier 264. The controller 32 may therefore determine the position of the filter member 260 by determining a position of the filter carrier 264 via the encoder 290. It is understood, however, that the encoder 290 may be any appropriate encoder such as an optical encoder, rotary encoder, or alternative linear encoder. Further, optical and magnetic technology may be used as an alternative or in addition to an inductive encoder.

Moving the filter member 260 in a linear manner via an appropriate filter carrier 264 may also be performed with other linear motors such as a lead screw or ball screw, a balanced linear motor, a worm screw, or other appropriate drive mechanism. Further, it will be understood that a linear motor, according to various embodiments, may include the drive coil 274 which moves and the magnet 276 that is fixed. In a moving coil assembly, the filter carrier 264 may be mounted on the drive coil 274 and the magnetic 276 be fixed to a mounting portion such as the mounting plate 278 or the bearings 280.

Figure 5:
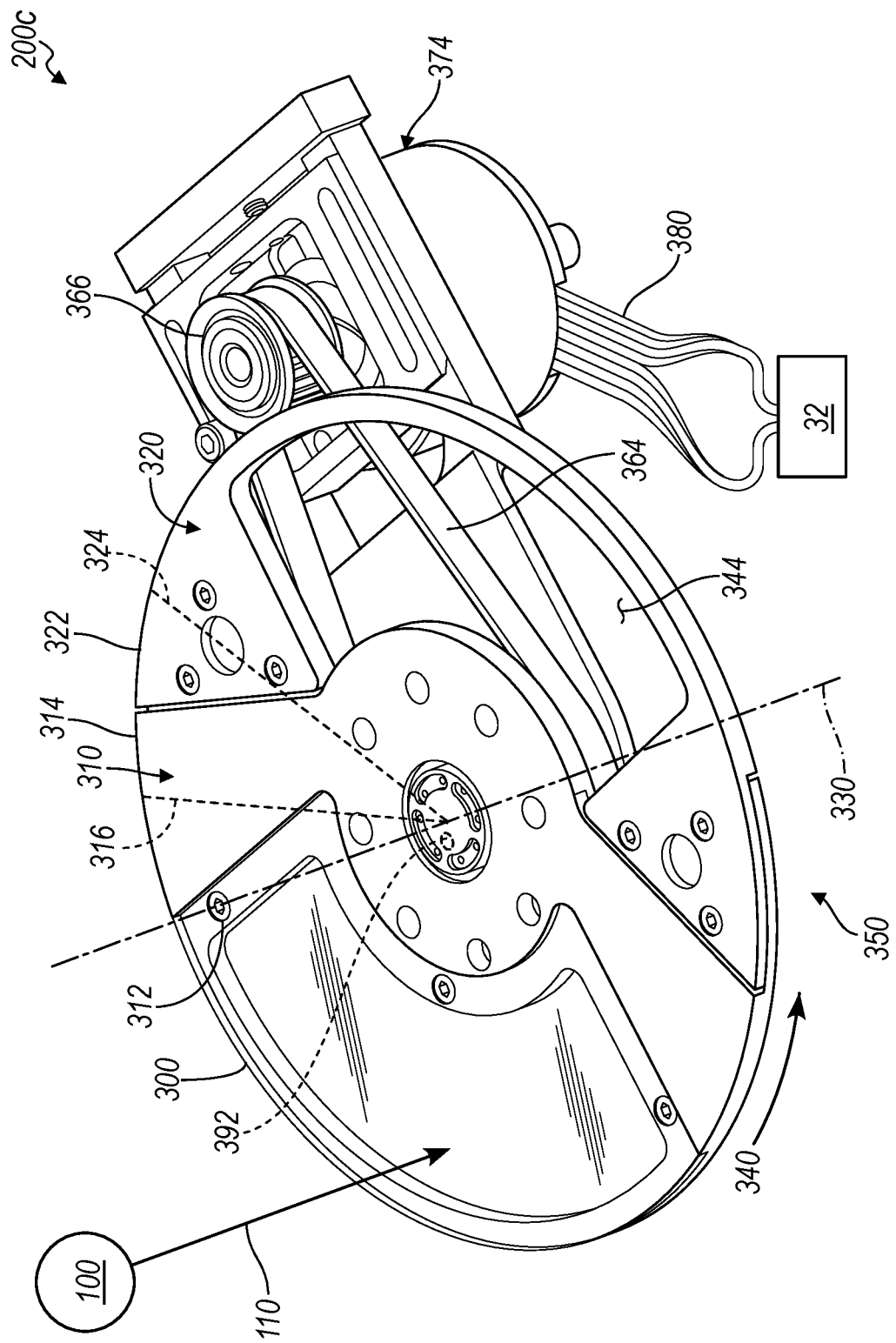
FIG. 5 is a detailed view of a filter assembly, according to various embodiments.

With reference to FIG. 5 a filter assembly 200c is illustrated. The filter assembly 200c may include a filter member 300 that is carried by a filter carrier 310, wherein the filter carrier 310 may rotate around an axis on a shaft. The filter member 300 may be formed of a selected material, including those discussed above, and fixed to the filter carrier 310. For example, bores may be formed in the filter member 300 and one or more screws 312 fix the filter member 300 to the filter carrier 310 by passing through or engaging the filter member 300 and the filter carrier 310. It is understood that other fixation mechanisms may be provided, such as welding, adhesives, brazing, or the like, to fix the filter member 300 to the filter carrier 310. The carrier 310 may further be provided as a frame such that x-rays that pass through the filter member 300 and reach the detector pass through the filter member 300, but not the material of the filter carrier 310.

As illustrated in FIG. 5 the filter carrier 310 may have a curved outer edge 314 such that the filter carrier 310 includes a radius 316 and has an outer arcuate edge 314. The filter carrier 310, therefore, may form at least a part of a circle or round member. The combination of the filter carrier 310 and the filter member 300 may have a selected mass that defines or forms only a portion of a circle. Therefore, a counterbalance 320 may be fixed to the filter carrier 310 to counter balance the mass of the filter member 300 and the filter carrier 310.

The counter balance may have an arcuate outer edge 322 and a substantially similar radius 324 to the radius 316. The counter balance 320, therefore, may form with the filter carrier 310 a circle. The counterbalance 320 and the filter carrier 310 form a filter carrier assembly 350 to move the filter member 300 relative to the x-ray to be positioned into or out of the x-rays generally travelling along the direction 110, as schematically illustrated in FIG. 5.

The filter carrier 310 may rotate around a shaft that has or forms a central axis 330. The filter carrier 310 may be operated to rotate in two directions or in a single direction, such as in the direction of arrow 340 around the axis 330. In various embodiments, the filter carrier 310 may be moved to carry the filter member 300 in substantially one rotational directional.

According to various embodiments the filter carrier 310 may be operated to rotate around the axis 330 at a substantially constant speed and rotation per minute (RPM). Therefore, whether the filter member 300 is in the beam path 110 or an open area of the filter carrier assembly 350 in the beam path 110. As the filter carrier 310 rotates around the axis 330 in the direction of arrow 340 in open air or void region 344, formed at least in part by the counter balance 320, may also be spaced or positioned in the beam path 110. Therefore, the rotation of the filter carrier 310 around the axis 330 can alternately place the filter member 300 in the beam path 110 or the void 344 in the beam path 110. It is understood, however, that the filter member 300 may have a size and moving the filter member 300 cause a void to be in the beam path, thus forming a void with a counter balance 320 is not required.

The filter carrier 310 on the assembly may need to rotate, such in the direction of arrow 340, at a selected rate to ensure that the filter member 300 is in the beam path 110 at a selected time. In this manner, the imaging with a filter and without a filter may be gated and controlled by the controller 32. Gating may be based upon various and/or predetermined factors such as energy selection of the x-rays, contrast agent injection, patient physiological motion (e.g. respiration or heart beat). As discussed above the filter member 300 may be positioned in a selected position in the beam path 110 to filter a selected portion of x-ray spectra of at least one of the emissions of x-rays at one of the energies of the dual x-ray imaging system at a selected time. As discussed above, it may be selected to switch the energies for generating x-rays of the imaging system at a frequency of about 30 Hz. Therefore, moving the filter member into and out of the beam may occur at about 33 milliseconds.

As illustrated in FIG. 5, the filter member 300 may be on one side of the filter carrier assembly 350 and may form about one-half of the circumference of a disk, therefore a one-half revolution of the filter carrier assembly 350 may be required to ensure movement of the filter member 300 into a first position in the x-ray beam along the vector 110 and movement to a second position that is out of the beam of the x-rays along the vector 110. Therefore, approximately 900 rotations per minute may be selected to achieve movement into and out of the beam at a rate to match the switching of the x-ray tube 100.

Figure 6:
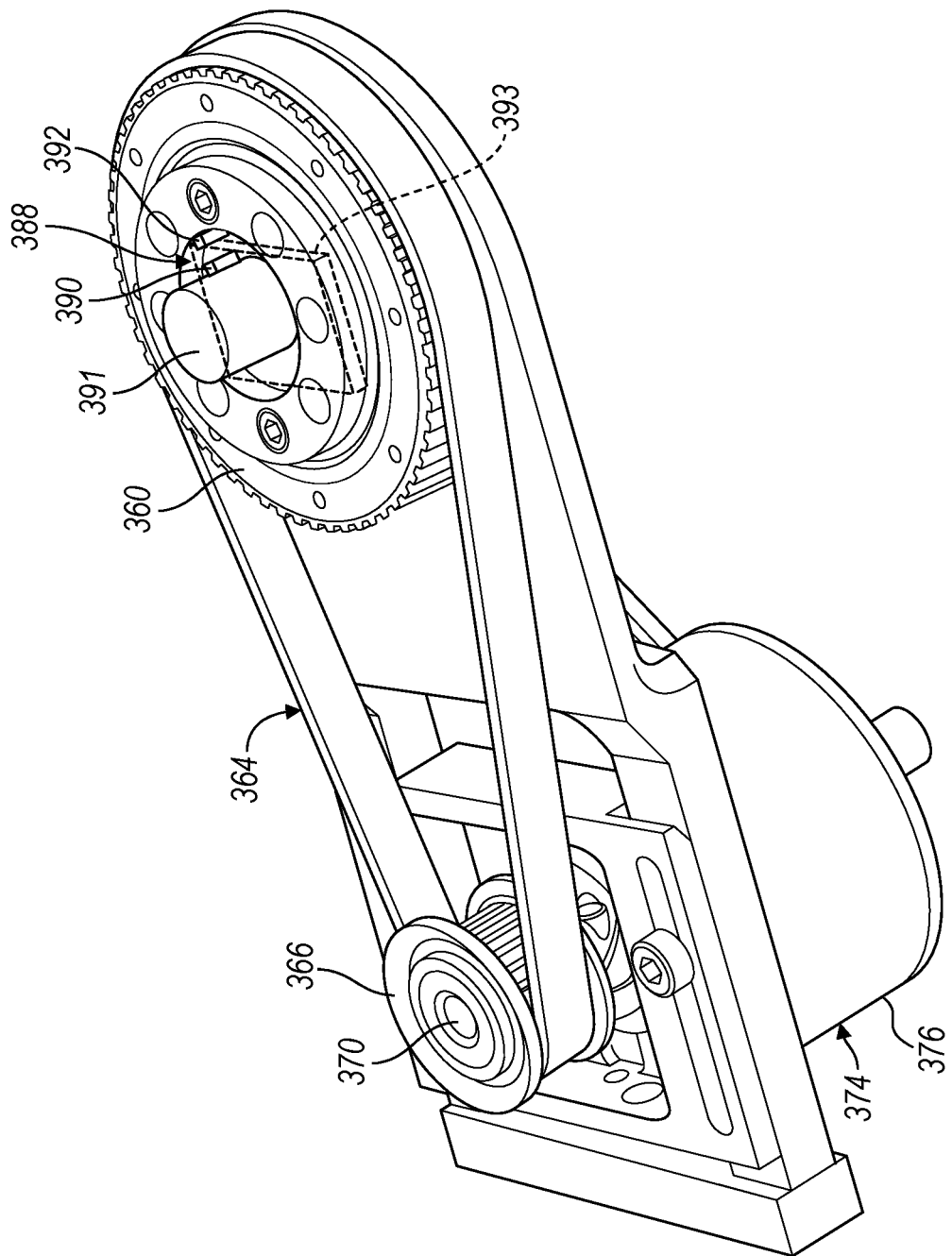
FIG. 6 is a perspective view of a drive assembly for the filter assembly illustrated in FIG. 5.

With continuing reference to FIG. 5 and additional reference to FIG. 6, the filter carrier assembly 350 may be connected to a carry gear 360, where the filter carrier assembly 350 is removed in FIG. 6 for clarity of the following discussion. The carry gear 360, in various embodiments, is driven by a belt 364 that is driven by a drive gear 366 that is connected to a shaft 370 powered by a motor assembly 374. The motor assembly 374 may include a housing 376 and a powered motor (not specifically illustrated) within the housing 376. The motor assembly 374 may be powered by various power mechanisms, such as electrical power, pneumatic power, or the like. The motor assembly 374 may be any appropriate motor assembly that can drive the filter carrier assembly 350 at the selected speed and be powered by the imaging system 16 and controlled by the controller 32. The motor assembly 374 may include an appropriate stepper and/or servo motors, for example the Maxon® EC-I-40 brushless DC servo motor sold by Maxon Motor Ag having a place of business in Switzerland.

Control connection 380 may be provided and interconnected with the imaging system controller 32. As discussed above, the positioning of the filter member 300 may be controlled by the imaging system controller 32 to filter x-ray spectra, as discussed above. The filter member carrier assembly 350 may be mounted to the carry gear 360 through the appropriate mechanism, such as one or more screws, bolts, adhesives, rivets, or other appropriate mechanical or chemical adhesions of the carrier assembly 350 to the carry gear 360. Therefore, upon rotation of the drive gear 366 the belt 364 may drive the carry gear 366 to spin the filter carrier assembly 350, including the filter member 300, at a selected rotation rate. It is understood, however, that the motor assembly 374 may be directly connected to the carry gear 360 without requiring the belt 364. In a direct connection, for example, the carry gear 360 may be mounted directly to the shaft 370 (e.g. replacing the drive gear 366) and/or the carry gear 360 may directly engage the drive gear 366 without the belt 364 and/or other transmission system. Alternatively, other appropriate drive or transmission mechanisms may be provided between the drive gear 366 and the carry gear 360 such as a worm drive, a geared transmission, or other appropriate connection systems.

During operation, the position of the filter member 300 may be synced with the location of the beam 110 in time with the emission of the x-rays at the selected power that are intended or selected to pass through the filter member 300 before reaching the patient 14. According to various embodiments the filter assembly 200c may include an encoder assembly 388. The encoder assembly 388 may include a magnetic encoder that may include a sensing magnet portion 390 and a transmitting magnetic portion 392. The encoder assembly 388 may be positioned near or at the carrying gear 360 such that it is positioned at the location of the filter member 300. For example, the sending magnet portion 392 can be positioned at a location that is adjacent or near the filter member 300. Therefore, when the magnetic portion 392 passes the reading portion 390 an index signal may be transmitted that the filter member 300 is the location of the beam 110.

The encoder assembly 388 may additionally and/or alternatively include a magnetic encoder such as the RMB20 magnetic encoder module and magnet sold by Renishaw having a place of business in West Dundee, Ill., U.S.A. In such a system the magnetic encoder 388 may include a magnet 391 that is incorporated into or in place of an axle to which the magnet 390 may be otherwise connected. The magnet 391 may rotate with the carrier gear 360 as the filter member 300 rotates. As the magnet 391 rotates a magnetic field produced by the magnet 391 moves relative to an integrated circuit encoder assembly that may be included on an integrated circuit or printed circuit board assembly system 393 that is fixed relative to the carrier gear 360 and the magnet 391. As is understood by one skilled in the art, the integrated circuit system 393 can sense the moving magnetic field of the magnet 391 to determine the index signal as discussed herein. Therefore, the encoder assembly 393 may act as the sending portion 392 or alternatively thereto.

Accordingly, it is understood by one skilled in the art that the encoder assembly 388 may be provided in any appropriate format including the magnet 391 and encoder assembly 393 as a noncontact magnetic encoder.

During operation, the filter assembly 200c may be operated or controlled such that the movement of the filter carrying member 310 is constant and synced in time to the emission of the selected x-rays along the x-ray beam 110. Direct control of the motor assembly 374 with the image controller 32 can ensure that the filter member 300 is positioned in the beam of the selected time to filter the x-rays emitted from the x-ray tube 100.

In an alternative and/or additional synchronizing method, the motor assembly 374 may be powered to turn the filter carrier assembly 350 at a nominal speed such that the filter carrier assembly 350 may rotate at about 900 RPMs, as discussed above. In various embodiments, a gear ratio between the motor assembly 374 and the carrier gear 360 is 3:1, thus the motor may rotate at about 2700 RPMs to cause rotation of the filter carrier assembly at about 900 RPMs.

Figure 7:
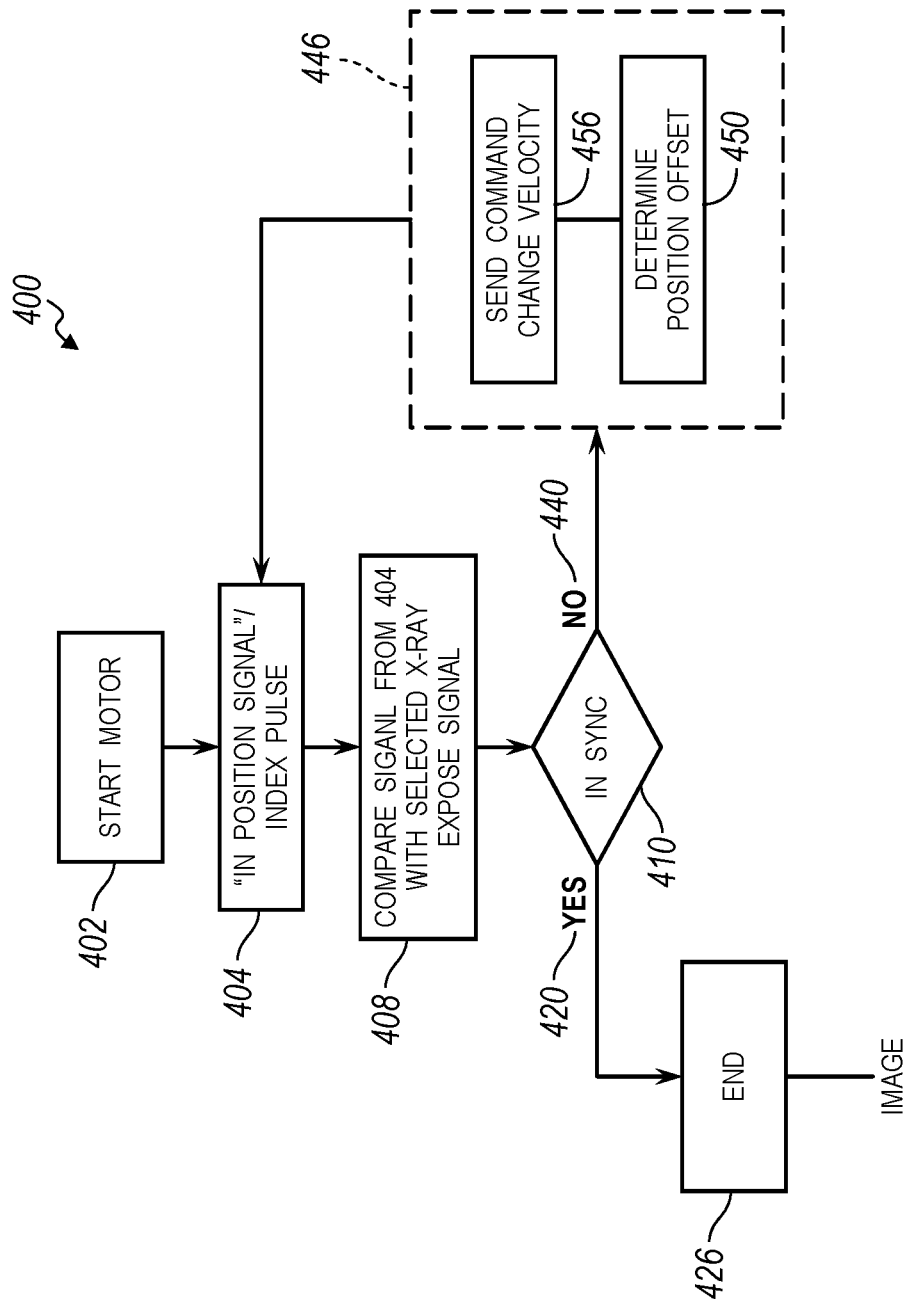
FIG. 7 is a flowchart of a synchronization method.

The encoder assembly 388 can be positioned and incorporated such that a single pulse signal is provided as the carrier assembly 350 rotates on the carrier gear 360. The index impulse may be aligned with the position of the beam 110 in the imaging system 16. Therefore, an indication or signal of when the filter member 300 is positioned in the beam 110 may be determined based upon an index pulse. To ensure that the filter member 300 is positioned at the beam 110 at the selected time, a synchronization process 400, as illustrated in FIG. 7, may occur once at start-up of the imaging system 16 or at a selected rate during imaging to ensure constant synchronization. As discussed above, the controller 32 may include a memory with a predetermined imaging protocol (including timing of imaging, number of image projections, etc.) and a related timing for operating the motor assembly 370 to move the filter carrier assembly 350. Further, the synchronization process 400 may be encoded as instructions to be recalled from the memory and executed by the processor.

Initially, the motor may be started in block 402 to initiate rotation of the filter carrier assembly 350 at the selected constant speed, such as about 900 RPMs. After starting the motor and rotating the filter carrier assembly 350, an in-position or index pulse can be received by the controller 32 in block 404. The in-position or index pulse, as noted above, can occur as the sending portion 392 passes the receiver portion 390 at the location of the beam 110, thus signaling that the filter member 300 is in position relative to the beam 110 and would filter x-rays, if x-rays were being emitted. The signal from block 404 can then be compared with a selected x-ray exposure signal in block 408. As noted above, the x-ray exposure may switch between at least two energies in a dual energy system at a selected rate, such as about 30 Hz. Therefore, the in-position signal when the filter member 300 is in position relative to the x-ray beam 110 can be compared to the appropriate timing or frequency of the selected x-ray emission.

A decision block of "in sync" 410 can be used to determine whether the filter member 300 is in sync with the selected x-ray emission timing and signal by the comparison in block 408. If it is determined in block 410 that the filter member 300 is in sync, then a YES path 420 may be passed to end the synchronization procedure in END block 426. The speed of the movement, including rotation, of the filer carrier assembly 350 may not change, therefore. Following the ending of the synchronization procedure 400, imaging may occur according to the selected imaging procedure, such as controlled by the controller 32, at the selected constant speed.

If synchronization is determined to not have occurred, a NOT path 440 may be followed to a synchronization procedure 446. The synchronization procedure 446 may include various steps such as determining a position offset in block 450. After determining a position offset, a send command to change velocity in block 456 may be made. The send command to change velocity in block 456 may be sent by the imaging system controller 32.

The send command to change velocity may increase or otherwise change the velocity of the carrier assembly 350 from the selected constant speed. For example, the speed may be increased from 900 RPMs to about 1000 RPMs, or about 2000 RPMs, or any selected speed. The velocity change may be for a selected period of time to correct for the position offset to achieve alignment or synchronization of the phase of the position of the filter member 300 with the timing of the emission of the x-rays. For example, the speed of the motor assembly 374 may be increased by a selected amount to position the filter member 300 within the x-ray beam 110 at the timing signal or emission signal for the x-rays at the appropriate time.

After a selected period of time, such as included in the send command to change velocity command block 456, the velocity of the filter carrier assembly 350 may be returned to the selected constant velocity, such as about 900 RPMs. The method may then return to block 404 and an in position signal may again be received from block 404. A comparison to the emission timing signal in block 408 may then occur. Thus, the in sync determination of block 410 can be determined. If it is determined that the carrier assembly 350 remains out of sync, the NO path 440 can be again used to attempt to achieve synchronization in block 446. However, if synchronization is determined, YES path 420 can be followed to the end block 426 and the constant speed may be maintained. Thus, the synchronization process 400 may be used in a loop to achieve synchronization of the position of the filter member 300 in the beam 110 at the time of emission of x-rays.

Accordingly, the motor assembly 374 may be operated to achieve synchronized rotation of the carrier assembly 350 with timing of the x-ray emission without rigid and direct continuous control of the motor assembly via a controller, including the image controller 32. The motor assembly 374 may, therefore, be operated to position the filter member 300 and beam 110 at an appropriate time using a synchronization technique, including the synchronization method 400 discussed above, and rotating the filter carrier assembly 350 at a constant rate.

Figure 8:
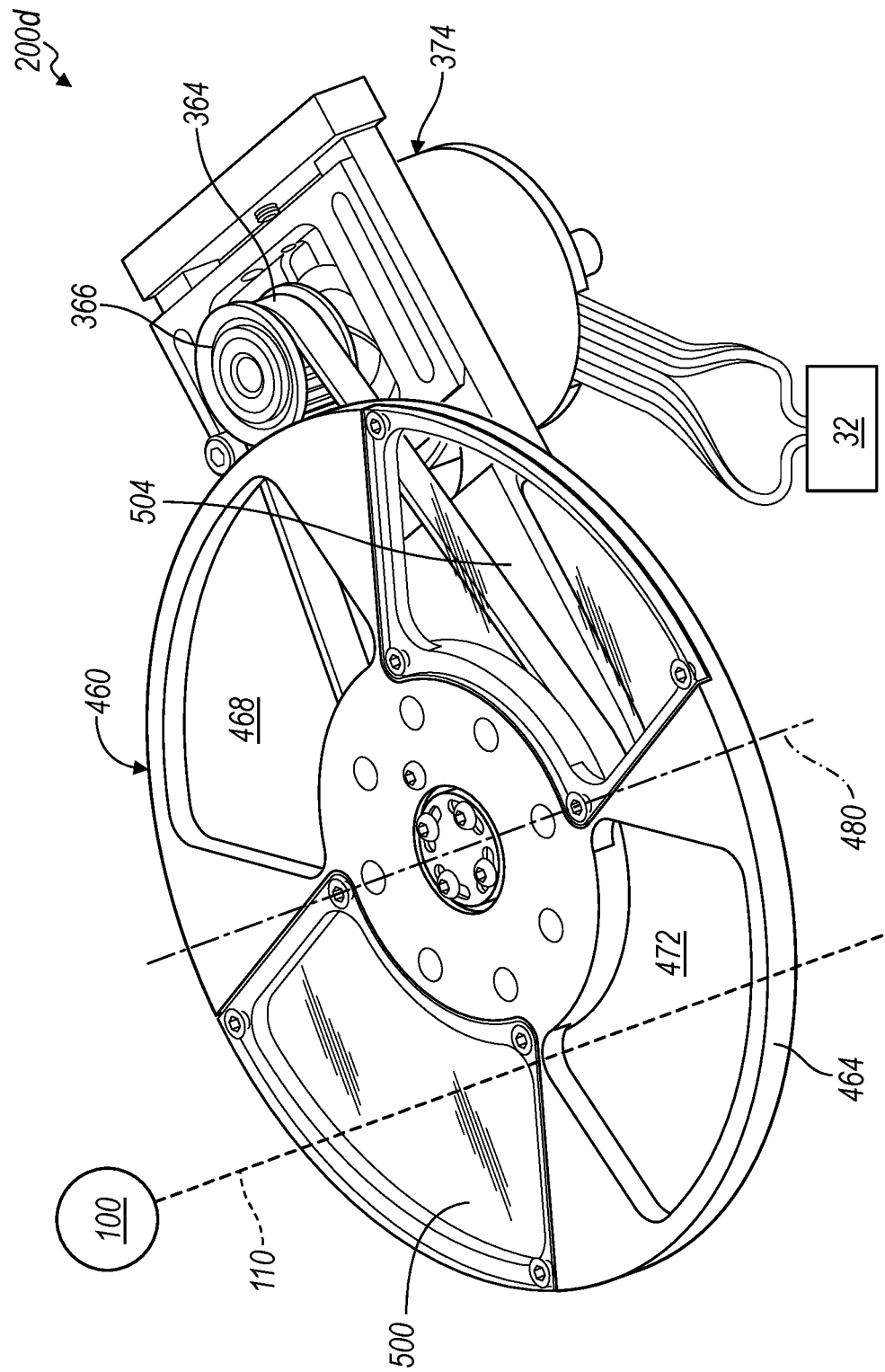
FIG. 8 is a detailed view of a filter assembly, according to various embodiments.

Turning reference to FIG. 8, a filter assembly 200d may include a filter carrier assembly 460. The filter carrier assembly 460 may be similar to the filter carrier assembly 350 of the filter assembly 200c illustrated in FIG. 5. Thus, the filter carrier assembly 460 may include a generally circular member having an outer curved edge 464. The filter carrier assembly 460 may differ, however, by having a first void 468 substantially opposed to a second void 472 at about 180° from each other around an axis of rotation 480. The filter carrier assembly 460 may also include two filter members including a first filter member 500 and a second filter member 504. Each of the filter members may be positioned about 180° apart around the axis of rotation 480. Further, the voids 468 and 472 may be positioned at generally 90° offset from the filter members 500 and 504 around the axis of rotation 480. The axis of rotation 480 may be similar to the axis of rotation 330, as discussed above and illustrated in FIG. 5, as the carrier assembly 460 may be mounted on the carrier gear 360 of the drive assembly illustrated in FIG. 6. Accordingly, the filter carrier assembly 460 may replace the filter carrier assembly 350 discussed above.

Accordingly, the filter carrier assembly 460 may alternatively include a filter member and a void at 90° around the axis of rotation 480. The operation of the filter carrier assembly 460 may be similar to the filter carrier assembly 350, as discussed above. However, the positioning of two filter members about 180° from another may allow the rotational speed of the filter carrier assembly 460 to be about one half that of filter carrier assembly 350. Accordingly the rotational speed of the filter carrier assembly 460 may be about 450 RPMs rather than about 900 RPMs. As one skilled in the art will understand, the filter member 500 or 504 would be positioned in the beam line 110 at about twice the rate as a single filter member, such as a single filter member 300. Therefore the filter member assembly 460 may rotate at substantially half the speed of the filter member assembly 350.

However, the speed or frequency of operation of the filter carrier assemblies 350 or 460 may be substantially constant during operation once a selected speed is reached. Therefore, as the carrier assemblies 350, 460 achieve the appropriate operational speed the speed may be maintained and the filter members will be positioned into and out of the beam 110 at an appropriate time.

Further, the synchronization of the filter carrier assembly 460 may occur in a manner similar to that discussed above, such as by the synchronization method 400. An index signal may be received when one of the filter members 500, 504 is within or at an in position that intersects the beam vector 110. The position of the other filter member is substantially 180° from the indexed filter member, therefore, the synchronization will be achieved as the slower speed of the filter carrier 460 ensures that the opposite filter member will reach the beam 110 at the appropriate time even if synchronization is made relative to only one of the filter members. Therefore, the filter carrier assembly 460 may be operated at a speed of substantially half that of the filter carrier assembly 350, while synchronization and a constant speed may still be performed and maintained in the manner similar to that described above.

Accordingly, according to various embodiments, a filter member may be positioned in the x-ray beam 110 to assist in achieving a selected spectra to reach the patient 14. Operation of the imaging system 16, therefore, may be used to achieve contrast enhancement of selected tissues or materials, such as two different soft tissues, hard tissue and soft tissue, contrast agent and other materials, metal and bone, or other selected differing materials. The filter member may be positioned into and out of the x-ray beam 110 according to various mechanisms, including those discussed above, to achieve further separation of the x-ray spectra at the differing energies.

It will also be understood that the image data and/or model can be used to plan or confirm a result of a procedure without requiring or using navigation and tracking. The image data can be acquired to assist in a procedure, such as an implant placement. Also, the image data can be used to identify blockages in the vasculature of the patient 14, such as with the contrast agent. Thus, navigation and tracking are not required to use the image data in a procedure.

According to various embodiments, as discussed above, a filter assembly may be included in a collimator 198 that may be positioned between the x-ray source 100 and the subject 14. As schematically illustrated in FIG. 2, and discussed above, the collimator 198 may include various features and portions, such as the filter 200, according to various embodiments, as discussed above. With additional reference to FIG. 9, the collimator 198 may include filters, as discussed above, and various other portions or systems in addition to the filters, according to various embodiments.

Figure 9:
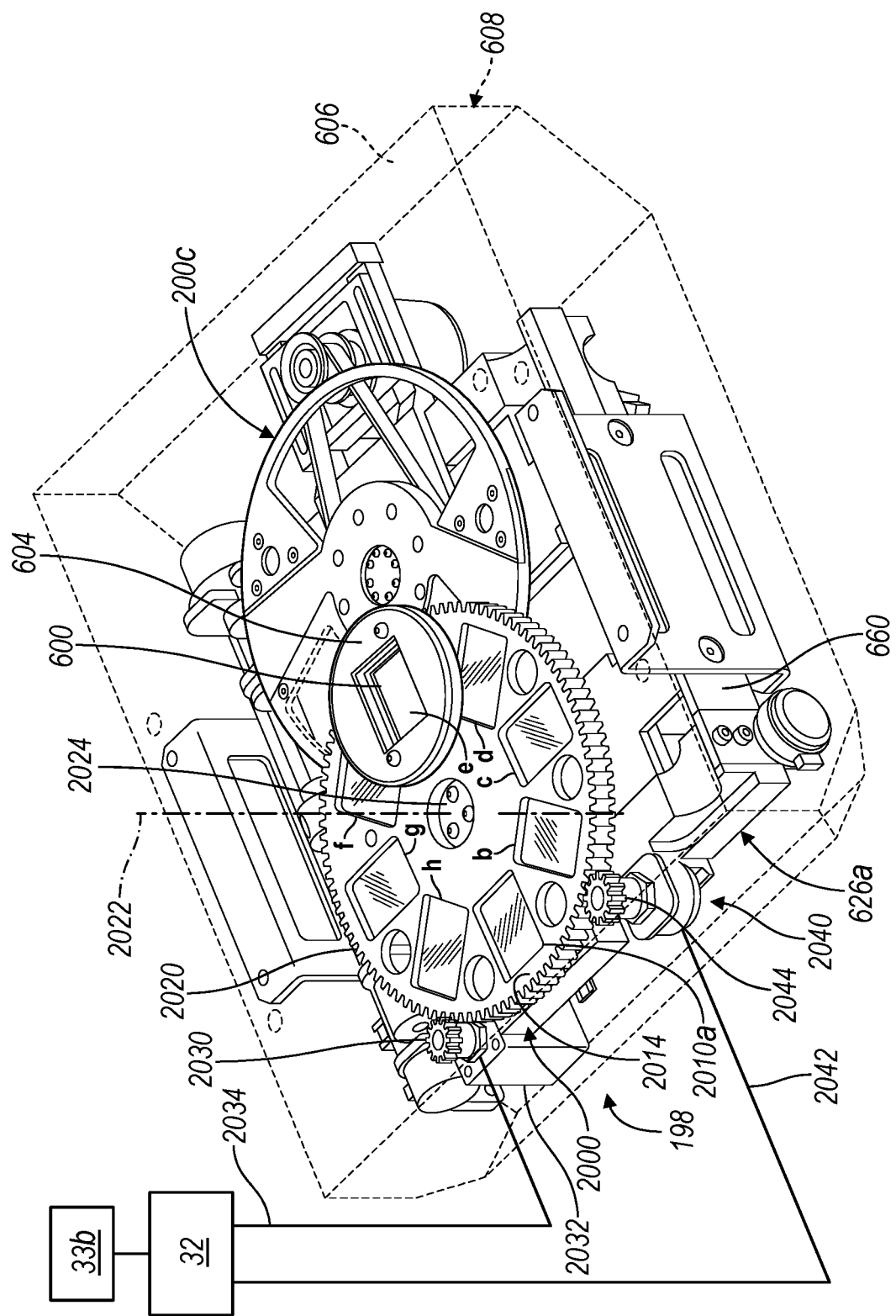
FIG. 9 is a view of a multiple-axis collimator assembly, according to various embodiments.

As illustrated in FIG. 9, the collimator 198 may also include various systems or features to selectively allow x-rays to pass through an exposure opening 600 of the collimator 198. The exposure opening 600 may be formed as a passage through an exposure ring or exposure member 604. The exposure ring 604 may be formed of a selected material, such a material that is opaque to x-rays. Accordingly, the exposure opening 600 may provide the only passage for x-rays out of the collimator 198 towards the subject 14.

The exposure ring 604 may be formed on a housing member 606 of the collimator 198. Generally, the housing member 606 may be part of a housing 608 that encompasses moving portions of the collimator 198 and allows it to be interconnected with various features, such as the x-ray source 100. The collimator may include the filter 200, such as the filter 200d, as discussed above. Further, the collimator 198 may be mounted on the housing 608 which, in turn, is mounted to the x-ray source 100.

In various embodiments, the collimator 198 can include various portions to allow altering a size or shape of the x-ray beam or cone 108. For example, the exposure opening 600 may include a maximum dimension of the x-rays that may exit the collimator 198, such as 3 cm×3 cm. Various radio opaque leaves, however, that form an axis selection assembly may be moved relative to the exposure opening 600 to alter the size of a cone of x-rays that will pass through the exposure opening 600 and, also may position the x-ray beam relative to the exposure opening 600.

Figure 10A:
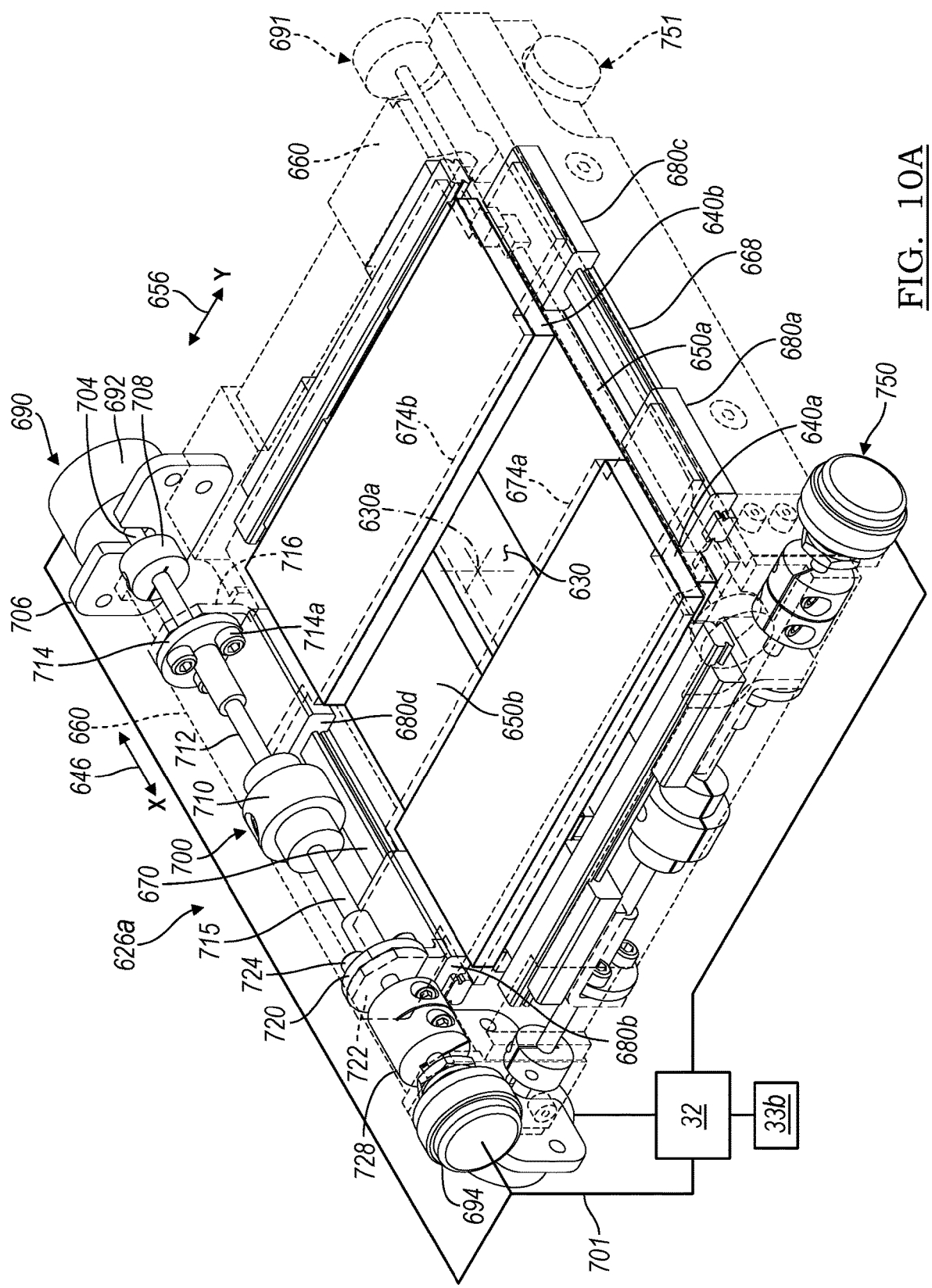
FIG. 10A is a first perspective view of a X and Y axis selection assembly for the multiple-axis collimator assembly, according to various embodiments.
Figure 10B:
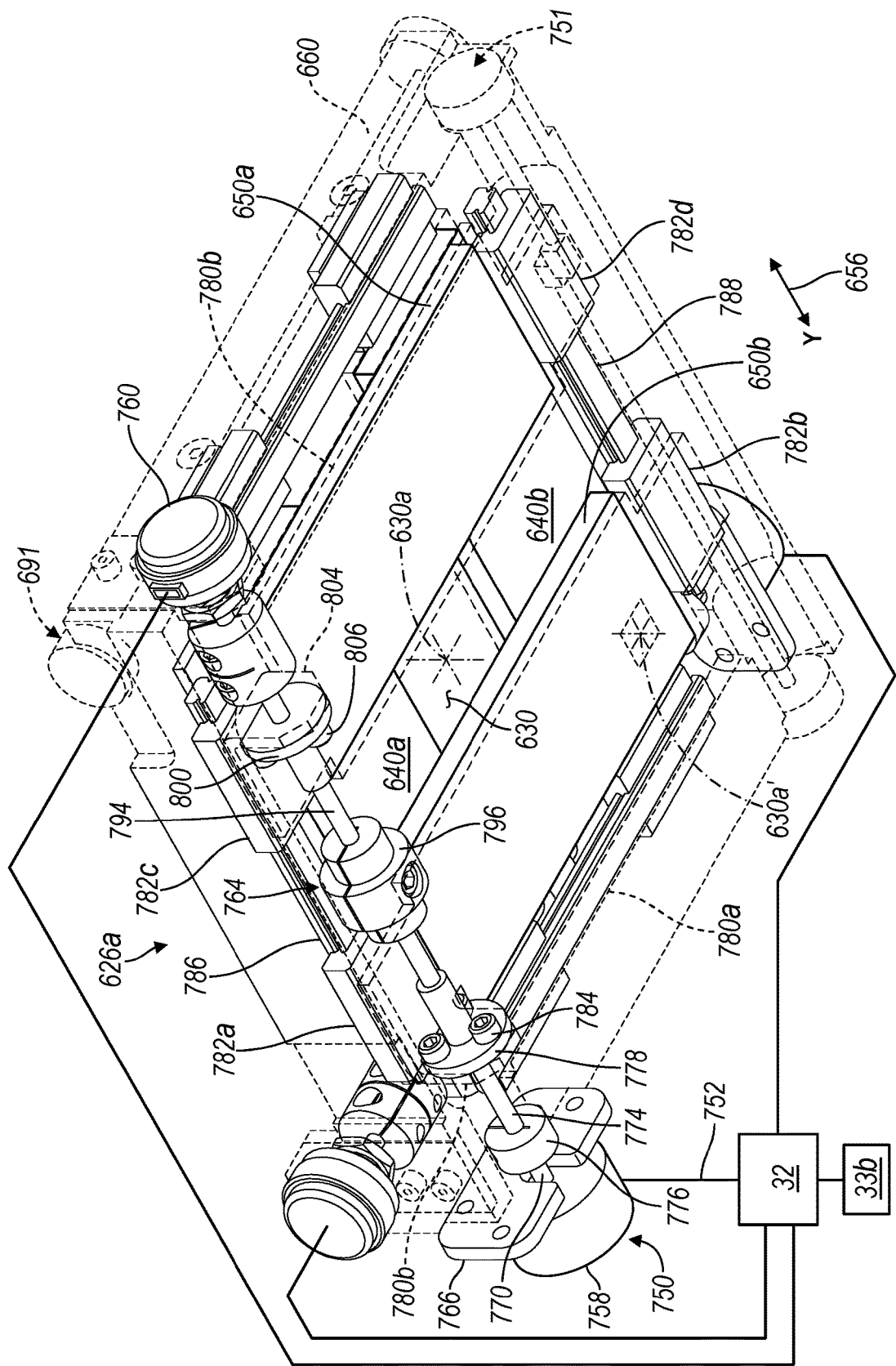
FIG. 10B is a second perspective view of the X and Y axis selection assembly of FIG. 10A for the multiple-axis collimator assembly, according to various embodiments.

With continuing reference to FIG. 9 and additional reference to FIG. 10A and FIG. 10B, an axis selection assembly (ASA) 626a, according to various embodiments is illustrated. The ASA 626a is positioned within the housing 608 of the collimator 198. The ASA 626a may include one or more leaves that are configured to move relative to the exposure opening 600 to select a size and/or location of a selected opening 630 to be formed relative to the exposure opening 600. The selected opening 630 is an opening through which the x-rays from the x-ray beam 108 is allowed to pass before exposing the subject 14. The selected opening 630 may be formed before or after the x-ray beam has passed other selected filters or axes, such as the high speed filter 200c.

The ASA 626a that includes a plurality of leaves that are able to move relative to one another on respective X-axis and Y-axis of movement relative to the exposure opening 600. For example, as illustrated in FIG. 10A, a first leaf 640a and a second leaf 640b may move opposed to each other and move in an X-axis generally in the direction of the double-headed arrow 646. A further pair of leaves may include a third leaf 650a and a fourth leaf 650b that may move in a Y-axis generally in the direction of the double-headed arrow 656. Accordingly, the leaves 640 and 650 may move relative and/or perpendicular to one another to form the selected opening 630 relative to the collimator exposure opening 600.

The selected opening 630 may be formed in substantially any location relative to the exposure opening 600 by selectively moving the leaves 640, 650 relative to one another.

Movement of the leaves, discussed further herein, may be based upon instructions that may be stored in a memory 33b that may communicate through various communication systems, such as wired, wireless, physical media, or the like, by the controller 32 to transmit instructions to move the leaves 640, 650. By moving the leaves, it is understood that the selected opening 630 may be formed in selected shapes, selected sizes, and selected positions relative to the exposure opening 600. Therefore, it is understood that the selected opening 630, as illustrated in FIGS. 10A and 10B, is merely exemplary and not intended to limit the possible selected openings.

Each of the leaves 640, 650 may be formed of a selected material, such as a high Z material (e.g. a material with a high effective Z number or high atomic number). For example, the leaves may be formed of lead of a selected thickness. The leaves may be formed so that the detector substantially only receives or detects x-rays that pass through the selected opening 630. Therefore, the leaves 640 and 650 may be moved to selectively create the selected opening 630 at a selected size and position for exposing the subject 14 to x-rays from the source 100.

The ASA 626a, including the leaves 640, 650, may include a frame portion 660. The frame 660 may be formed as a single piece, or formed as a plurality of pieces. The frame 660, for example, may be formed as a single cast piece or member onto which the selected portions of the leaves and other elements are positioned. Alternatively, or in addition to a single member, various pieces may be interconnected such as with welding, raising, or other fasteners. Additional brackets or fixation points may be included with the frame 660, as discussed herein.

Mounted to the frame 660 may be guide rails that assist in guiding the leaves 640, 650. For example, the X-axis leaves 640 may be interconnected with a first rail 668 and a second rail 670. The rails 668, 670 may be fixed to the frame 660 in a selected manner, such as with rivets, threaded screws, or the like. Further, the rails 668, 670 may be substantially parallel to one another. The rails 668, 670 allow the leaves 640 to move relative to one another substantially binding free and in a single plane. Further, the rails 668, 670 assist in maintaining straight and linear movement of the leaves 640.

The two leaves 640a, 640b may be fixed or mounted to leaf carriers 674a and 674b. Each of the carriers 674 may have fixed thereto one of the respective leaves 640a, 640b. Fixation of the leaves to the respective carrier 674 may be with braising, rivets, or other appropriate fixation mechanisms. The carriers 674a, 674b may extend to cars or sliding members 680a, 680b, 680c, 680d. Each of the carriers 674a, 674b may be fixed to two of the cars that are able to move on the rails 668, 670. As the carriers 674a, 674b move, the cars 680a-d may move along the respective rails 668, 670 and the carried leaves 640a, 640b may move generally in the direction of the double-headed arrow 646. The parallel rails 668, 670 allow for smooth and binding free movement of the leaves 674a, 674b relative to one another, and the frame 660. Further, the parallel rails 668, 670 allow for a driving mechanism 690 on a single end, and in various embodiments only the single end, of the carriers 674a, 674b and/or leaves, as illustrated in FIGS. 10A and 10B.

The drive mechanism 690 may include various portions such as a motor assembly 692, a sensor assembly, such as a position sensor 694, and a double lead screw assembly 700. The drive mechanism 690 may operate and be controlled by the controller 32 with a selected communication system 701 that may be provided to control the motor 692 of the drive mechanism 690 from the controller 32 and the communication system may receive sensed positions from the sensor 694. Further, the controller 32 may be operated by a user to selectively operate the motor 692 for various purposes during imaging of the subject. Therefore, the drive mechanism 690 to move the leaves 640a and 640b may be operated in an automatic manner based upon predetermined instructions, to form the selected opening 630, manually by a user such as during an imaging procedure, or a combination of both.

The motor 692 may be any appropriate type of motor such as a stepper motor, servo motor, or other appropriate type of motor. Generally, the motor 692 provides rotary motion to a drive shaft 704 which is connected to the screw assembly 700. The motor 692 may be mounted to a bracket 706 that may be fixed to the frame 660 or may be directly fixed to the frame 660. A connection portion, such as a split nut 708 may be used to connect to the drive shaft 704 to the screw assembly 700. The screw assembly 700 may further include a second split nut 710 that connects a first screw portion 712 to a second screw portion 715.

The first screw portion 712 may threadably engage a carrier holder 714. The carrier holder 714 may be fixed to a bracket or extension 716 of the leaf carrier 674b. The carrier holder 714 may be fixed to the bracket 716 in the appropriate manner, such as with one or more screws 714a. The screws 714a, however, may also be provided or included as rivets, nuts, or other appropriate connection mechanisms.

The carrier holder 714 may include an internal thread that is threaded in a first direction. Therefore, as the first screw portion 712 rotates within the carrier holder 714 an external thread on the first screw portion 712 may engage internal threads on the carrier holder 714 to move the leaf carrier 674b generally in the direction of the double-headed arrow 646.

The second screw section 715 may also include an external thread. The second screw section 715, connected to the first screw portion 712 through the split nut 710, receives a rotational force from the motor 692 via the first screw section 712. A second carrier holder 720 may include an internal thread that is in an opposite direction of the internal thread of the first carrier holder 714. Therefore, the first leaf carrier 674a may move opposite the direction of the second leaf carrier 674b, although the screw portions 712, 715 are rotating in the same direction.

The second carrier holder 720 may be fixed to a second extension or bracket portion 722 that extends from the carrier 674a. The second carrier holder 720 may be fixed to the extension 722 with one or more screws 724 similar to the screw 714a. The sensor 694 may sense motion or rotation of the screw portion 712, 715 to assist in determining the position of the leaves 640. The sensor 694 may be connected to the second screw portion 715 with a third split nut 728. The position sensor 694 may be any appropriate positions sensor, such as an optical shaft encoder including the US Digital® S4T optical shaft encoder (Part No. S4T-300-125-D-B) sold by US Digital, having a place of business in Vancouver, Wash., USA.

With continued reference to FIG. 10A and additional reference to FIG. 10B, the leaves 650a and 650b may be moved in the direction of the double-headed arrow 656 on the Y-axis in a manner substantially similar to the leaves 640a and 640b. The two leaves 650a, 650b may be connected, individually, to two leaf carriers 780a, 780b, in a manner similar to the leaves 640 connected to the leaf carriers 674, as discussed above.

The leaves 650 may be driven with a drive mechanism 750 similar to the drive mechanism 690, discussed above. A communication system 752 may connect a motor 758 and a position sensor 760 of the drive mechanism 750 with the controller 32. The controller 32, therefore, may operate or control both the motor 692 of the drive mechanism 690 and the motor 758 of the drive mechanism 750. Operation of the drive mechanism 750 is similar to the operation of the drive mechanism 690, therefore, its operation in part will not be discussed in detail, but disclosed briefly here with reference to FIG. 10B.

The drive mechanism 750 may include the motor 758, a sensor 760, and a lead screw mechanism 764. Therefore, the motor 758 may be fixed to a bracket 766 which is fixed to the frame 660 and/or fixed directly to the frame 660. A drive shaft 770 may be driven by the motor 758 which is connected to a first screw portion 774 by a split nut 776. The first screw portion 774 passes through a third carrier holder 778 to threadably engage the third carrier holder 778. The third carrier holder 778 has internal threads in a first direction to move the leaf carrier 780a to which the leaf 650b is connected. The leaf carrier 780a may include an extension 780b to which the third carrier holder 778 is connected such as with one or more screws 784. Further, the leaf carrier 780a may extend and interconnect with a car 782 that rides on a third rail 786. The leaf carrier 780a also extends to a car 782b that rides on a fourth rail 788. The rails 786, 788 may be substantially parallel similar to the rails 668, 672, discussed above, to allow for smooth and non-binding movement of the leaf 650b with the drive mechanism 750 at a single end, and in various embodiments only the single end, of the leaf 650b.

The first screw portion 774 is connected to a second screw portion 794 with a split nut 796. Other connections, either in addition or alternatively to the split nut 796 may be used, such as welding, adhesive materials, brazing, etc. Therefore, rotational motion of the first screw portion 774 is transferred to the second screw portion 794. The second screw portion includes external threads which engage internal threads in a fourth carrier holder 800. The internal threads in the fourth carrier holder 800 may be opposite those in the internal threads of the third carrier holder 778. The first and second screw portions 774 and 794 may have similar threads and an identical rotational direction of the screw portions 774, 794 will move the respective carrier holders 778 and 800 in opposite directions.

The fourth carrier holder 800 may be fixed to the fourth leaf carrier 780b through an extension or projection 804 with one or more screws or other fixation members 806, similar to the fixation members discussed above. The leaf carrier 780b may include portions that extend and connect to two cars 782c and 782d so that the leaf carrier 780b may ride along the rails 788 and 786 generally in the direction of double-headed arrow 656 in the Y axis. As discussed above, the rails 786, 788 assist in allowing movement of the leaf 650a in a smoothing, straight, and non-binding manner.

It is understood the drive mechanisms 690 and 750 may be provided at the single ends, and in various embodiments only single ends, of the respective leaves 640, 650 and through the interaction of the leaf carriers 674, 780 with the respective parallel rails 668, 670, 786 and 788, allow smooth and non-binding movement of the leaves 640, 650. It is further understood, however, that drive mechanisms may be provided at both ends of the respective leaf carriers to simultaneously drive both ends of the leaf carrier to assist in moving the leaves 640, 650 to selected positions and at a selected rate. In either instance, the leaves 640a, 640b may move at a similar or identical speed based on each other. Similarly, the leaves 650a, 650b may move at a similar or identical speed based on each other. Thus, the selected aperture 630 may be increased or decreased in size, but have a center 630a of the selected exposure be substantially unmoved regardless of size or shape of the selected aperture 630. Accordingly, the selected aperture 630 may be a square that is 1 inch by 1 inch that has the center 630a or the selected aperture 630 may be a rectangle that is 1 inch by 2 inches and would still maintain the center 630a.

In various embodiments, individual drive mechanisms, similar to the drive mechanism 690 or the drive mechanism 750, and may include drive mechanisms 691 and 751 (shown in phantom) may be connected individually to each of the leaves 640a, 640b, 650a, and 650b. Thus, each drive mechanism 690, 691, 750, 751 may be used to drive the respective individually each leaf 640a, 640b, 650a, and 650b on the respective X-axis or Y-axis. Each drive mechanism may connect or interact with a single leaf connector to engage and move the respective leaf. As each leaf 640a, 640b, 650a, and 650b moves independently, as operated by the controller 32, the selected opening 630 may have an independent size and the center 630a may move relative to the frame 660. Thus, it is understood that each of the individual leaves 640a, 640b, 650a, and 650b may be driven separately, in a manner similar to that described above, with an appropriate drive mechanism to select all of a shape and size of the selected opening 630 and a location of the center 630a, such as an alternative center location 630a'.

Accordingly, the ASA 626a may be positioned in the collimator 198 to form the selected exposure opening or aperture 630. The ASA 626a may be incorporated into the collimator 198 in any appropriate manner, including as illustrated in FIG. 9 as discussed above. It is understood, however, that the leaves that form the ASA may be moved in an appropriate manner including those discussed further herein.

Figure 11:
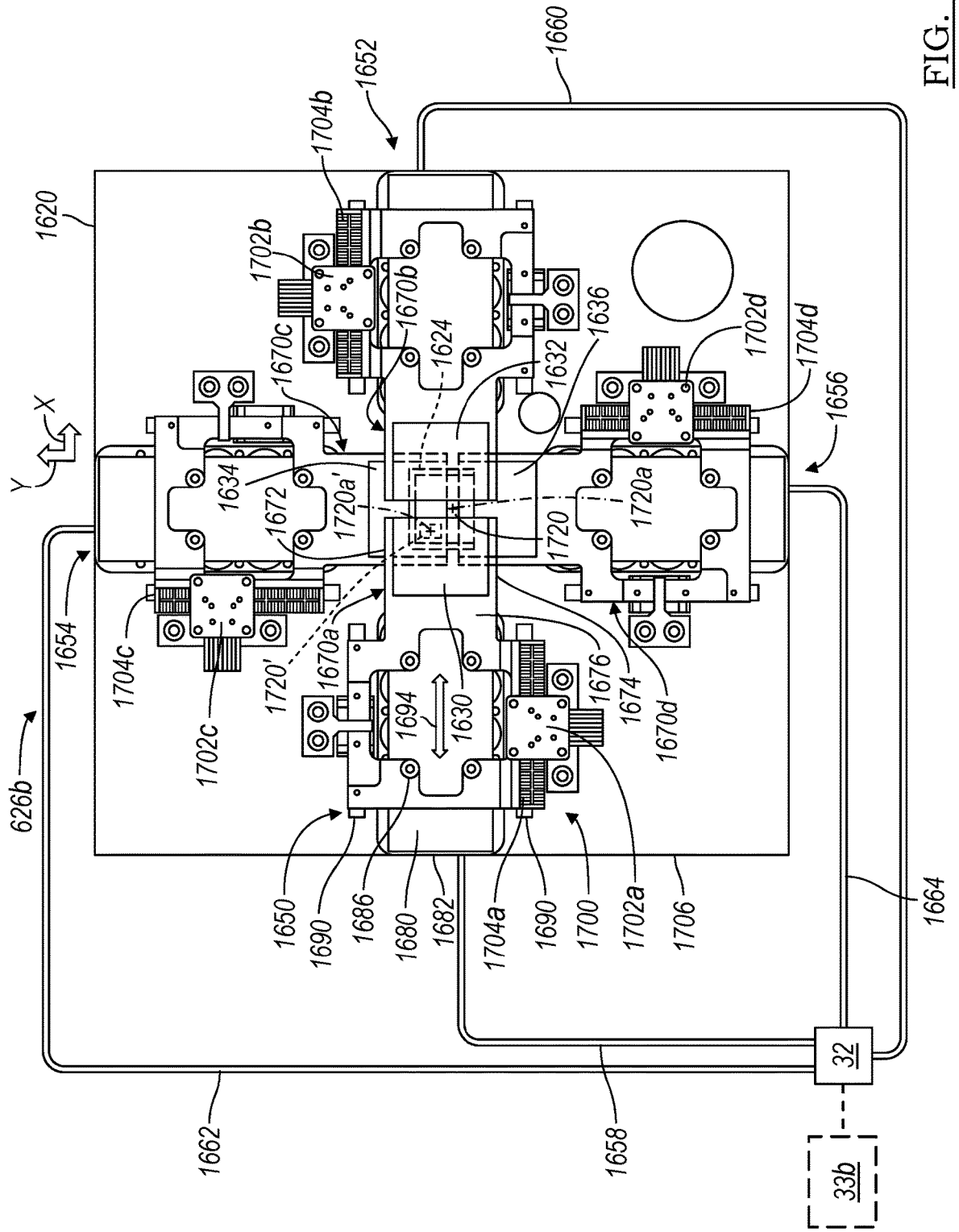
FIG. 11 is a plan view of a X and Y axis selection assembly for the multiple-axis collimator assembly, according to various embodiments.

In various embodiments, with reference to FIG. 11, the collimator 198 may include an ASA 626b that may include a stage or platform member 1620 which may include a stage exposure opening or passage 1624. The stage exposure opening 1624 may also be fixed in dimension by walls or edges through the stage 1620. The stage exposure opening 1624 may be of a selected size relative to the exposure opening 600, such as larger, smaller, or the same size. The stage exposure opening 1624 may be larger than the exposure opening 600 in various embodiments to ensure that all of the exposure opening 600 may be exposed to x-rays, if selected.

The ASA 626b may be provided in various embodiments, as discussed herein, to selectively size and position an opening formed by leaves relative to the stage exposure opening 1624. Thus, the stage exposure opening 1624 may define a maximum and/or fixed opening through the stage 1620 that may be altered by the ASA 626b. It is understood, however, that the stage 1620 may not include a small opening, but may include only an open or external frame (similar to the frame 660 discussed above) to which other portions are connected, as discussed herein.

In various embodiments, the ASA 626b includes a plurality of leaves, including a first leaf 1630, a second leaf 1632, a third leaf 1634, and a fourth leaf 1636. Each pair of the leaves, such as a first pair of leaves 1630, 1632 and a second pair of leaves 1634, 1636 may operate to adjust the beam of x-rays passing through the stage exposure 1624 in a X and/or Y axis. For example, the first pair of leaves 1630 and 1632 may move in an X-axis to change the beam of x-rays in the X axis while the second pair of leaves 1634, 1636 may move in a Y-axis to adjust the beam of x-rays through the exposure passage 1624 in a Y axis direction. As discussed further herein, the leaves 1630, 1632, 1634, 1636 may be operated to adjust a size, a position, or an orientation of a x-ray's beam passage through the exposure passage 1624, as selected by a user, programming of the x-ray exposure, selected energy of the x-ray beam, or the like.

Each of the leaves 1630, 1632, 1634, 1636 may be moved by a selected mechanism. For example, each leaf may be interconnected with a linear motor, similar to the linear motor 270 discussed above. For example, the first leaf 1630 may be interconnected with a first linear motor 1650, the second leaf 1632 may be interconnected with a second linear motor 1652, the third leaf 1634 may be interconnected with a third linear motor 1654, and the fourth leaf 1636 may be interconnected with a fourth linear motor 1656. Each of the linear motors 1650, 1652, 1654, and 1656 may be operated in a manner similar to the linear motor 270 discussed above to move the respective leaves 1630-1636 relative to the stage exposure passage 1624.

The linear motors 1650-1654 may be controlled by the control system 32 of the imaging system 16; the controller may include the processor 33a that is designed and/or configured to operate the linear motors 1650-1654 and/or execute instruction, such instructions stored on the memory system 33b. Each of the motors 1650-1656 may be individually connected through various communication lines, such as the respective communication lines 1658, 1660, 1662, and 1664. It is also understood that a communication system may be incorporated into the collimator 198 to communicate with the controller 32. The communication system may include various wireless communication protocols that may be used to wirelessly communicate with the controller 32 to operate the motors 1650-1656. As discussed herein, each of the motors 1650-1656 may be operated independently of one another to move the respective leaves 1630-1636 relative to the platform exposure 1624. It is further understood, however, that the respective motors may be operated as motor pairs. For example, the first motor 1650 and second motor 1652 may be operated as a pair to move the respective leaves 1630, 1632 relative to the passage 1624 while the third and fourth motors 1654, 1656 may be operated as a pair to move the respective leaves 1634, 1636 relative to the exposure passage 1624. When operated as a motor pair, a single signal may be sent to adjust a respective axis of the collimator (e.g., X axis or Y axis). The single signal may be to adjust the position (e.g., +2 mm). The motor pair may then operate both motors to achieve the adjustment. Generally, the motors 1650-1656 are operated to move respective leaves to and away from one another as a pair or as the group of four leaves 1630-1636.

With brief discussion of the first leaf 1630 and the first motor 1650, it is understood that the other leaves and motors may be configured substantially similar to the leaf 1630 and motor 1650 and will not be repeated in detail below. Generally, the leaf 1630 may be formed of a selected material that may be substantially radio opaque. That is, the leaf 1630 may be provided or formed of a material that will not allow x-rays to penetrate or substantially penetrate the leaf 1630 to expose the x-ray detector through the patient 14. For example, the leaf 1630 may be formed of lead having a selected thickness. Any appropriate high Z material, however, may be selected to form the leaf 1630. The leaf 1630 may be formed of a material in a selected dimension such that its mass may be moved at a selected rate by the motor 1650 relative to the exposure opening 1624.

The leaf 1630 may be positioned in a leaf carrier 1670 of the first motor 1650. The leaf carrier 1670 may include a first finger 1672 and a second finger 1674 that extend from a main carrier body 1676. The first and second fingers 1672, 1674 may define an opening or passage therethrough and the leaf 1630 may be positioned between the two fingers 1672, 1674 in the passage. The leaf 1630 may be fixed within the passage relative to the fingers 1672, 1674 in any appropriate manner such as with brazing, an adhesive, a mechanical fixator (e.g., a screw), or other appropriate mechanism.

The leaf carrier 1670 may be mounted to a moving magnet 1680. The moving magnet 1680 may be positioned over a stationary and/or linear motor coil 1682. As discussed above, the stationary linear motor coil 1682 (similar to the stationary linear motor coil 274 discussed above) may be operated to move the moving magnet 1680 (similar to the magnet 276, discussed above). It is further understood that various other configurations may be provided, such as a stationary magnet and moving linear motor coil or the like. Thus, the leaf carrier 1670 may be mounted to a moving coil that is moved relative to a fixed magnet.

The leaf carrier 1670 may be fixed to the moving magnet 1680 with various mechanisms. For example, a screw or rivet may be positioned through a fixation passage 1686 to fix the carrier 1670 to the magnet 1680. It is further understood that various pieces, welding, brazing, or the like may be used to fix the leaf carrier 1670 to the moving magnet 1680.

Further, the linear motor 1650 may include linear bearings 1690 on which the carrier 1670 moves. The linear bearings 1690 may bear the carrier 1670 and the attached moving magnet 1680 as they move. The bearings 1690 may also assist in directing movement of the linear motor 1650. Generally, the bearings 1690 may limit a movement of the moving magnet 1680, such as generally in the direction of the double-headed arrow 1694. The double-headed arrow 1694 may be along the X-axis, as discussed above, to move the leaf 1630 on the X-axis. A position of the carrier 1670 may be determined with a position determining system 1700 including a read head 1702 and a rail 1704. The read head 1702 may read a relative or absolute position of the carrier 1670 relative to the rail 1704, similar to operation of the read head 292 and the rail 294, as discussed above.

Accordingly, the operation of the linear motor 1650 to move the leaf 1630 may be similar to operation of movement of the linear motor 270 to move the filter 260. In particular, the leaf 1630 may be moved to be positioned into or out of at least a portion of the x-ray beam 108 moving along the vector path 110. As discussed further herein, the leaf 1630 may be used or operated to block at least a portion of the full emission of x-rays from the x-ray source 100 to configure or shape the beam passing through the platform exposure passage 1624.

As discussed above, each of the leaves 1630, 1632, 1634, and 1636 may be moved as respective pairs and/or moved independently to achieve a selected opening position and/or shape to allow x-rays to pass through the platform exposure passage 1624. As illustrated in FIG. 11, the leaves 1632 and 1630 may be the leaves that define the X axis position of a selected opening 1720. The leaves 1634, 1636 may be moved to change a Y axis position of the opening. As illustrated in FIG. 11, a shape of the selected opening 1720 is defined by all of the leaves 1630, 1632, 1634, and 1636.

As illustrated in FIG. 11, to allow for each one of the leaves 1630-1634 to move relative to one another, the opposing sets of the leaves may be offset a height relative to the other leaves. As illustrated, the pair of leaves 1630 and 1632 that move in the X-axis may be positioned further away from the stage 1620 than the opposed leaves 1634 and 1636 that may be positioned closer to the stage 1620 than the X axis leaves 1630, 1632. The positioning of the Y axis leaves 1634, 1636 closer to the stage 1620 may include forming an offset in the leaf carrier 1670c, 1670d to position them closer to the stage 1620 than the X axis leaves 1630, 1632. Alternatively, the X axis carrier 1670a and 1670d may be offset relative to the Y axis leaf carriers 1670c, 1670d. Regardless of the configuration, the leaves opposing one another to form the X and Y axis may be configured to allow them to move and be positioned simultaneously over at least a portion of the stage axis exposure 1624, as illustrated in FIG. 11.

Similar to the selected opening 630, discussed above, the selected opening 1720 may be any selected shape that may be defined by the leaves 1630-1636. Each of the leaves 1630-1636 may be moved independently and individual, similar to the leaves 640a, 640b, 650a, and 650b discussed above, for the selected opening 1720 to be selected to be square, rectangular, or other shape depending upon the geometry of the respective leaves 1630-1636. Further, the size of the selected opening 1720 may be selected based upon the relative position of the leaves 1630-1636.

Moreover, the position of the selected opening 1720, or a center 1720a of the selected opening 1720, may be selected also based upon the position of the leaves 1630-1636 relative to the stage exposure openings 1624. For example, the stage exposure opening 1624 may be a square, and the selected opening 1720, and/or the center 1720a, may be selectively positioned in a quadrant of the stage exposure opening 1624 such as a lower right quadrant. Further, however, the selected opening may be positioned in an upper left quadrant, as illustrated in phantom 1720' by moving the leaves 1630-1636 to form the selected opening 1720'. Thus, the selected opening 1720' may be a center 1720a' different than the center 1720a of the selected opening 1720. Further, the positioning of the leaves 1630-1636 relative to the stage exposure opening 1624 may selectively make the selected opening 1720 equal to the dimensions of the stage exposure 1624 or less than the full opening dimensions of the stage exposure opening 1624.

As discussed above, each of the leaves 1630-1636 may be moved by respective motors 1650-1656. The position of the leaf carrier 1670, for example carrying the leaf 1630, may be determined with the read head 1702 relative to the rail 1704. As discussed above, the position of the read head 1702 relative to the rail 1704 may be used to determine the position of the lead carrier 1670 in the manner similar to the determining of the position of the linear letter with read head 292 relative to the rail 294, as discussed above.

Each of the leaves may be held by respective leaf carriers including a leaf carrier 1670b to carry leaf 1632, leaf carrier 1670c to carry leaf 1634, and leaf carrier 1670d to carry leaf 1636. Each of the leaf carriers 1670a-1670d may have respective read heads 1702a-1702d that are fixed to the leaf carriers 1670a-1670d and move relative to respective rails 1704a-1704d. Communication line or system (e.g., either wired connections and/or wireless connections) 1658-1664 may communicate with a controller 32 to provide instructions to the linear motor 1650-1656 based upon the determined position of the leaf carriers 1670a-1670d based upon the read positions of the read heads 1702a-1702d relative to the rails 1704a-1704d.

The movement of the leaf carriers 1670a-1670d to move the respective leaves 1630-1636 may be based upon a predetermined program or set of instructions that are recalled from the memory 33b. It is further understood that the memory 33b may include instructions to determine a planned or selected movements for forming the selected exposure opening 1720 based upon instructions input by a user. Instructions input by a user may be selected or changed during a procedure based upon various aspects, such as experience of the user, expertise of the user, or other selected considerations. It is understood, however, that the movement of the selected opening 1720 may be predefined and varied relative to the stage exposure 1624 based upon a preselected positioning of the selected opening 1720. Further, given the four separate motors, each of the leaves may be moved independently (e.g. regarding direction along the respective X- and Y-axes and amount of movement) in the ASA 626b.

Further, as discussed above, the collimator 198 may be included in the imaging system 16. The imaging system 16 may include the source unit 36 that is able or configured to move relative to a selected gantry, such as the imaging gantry 34. Therefore, as the source unit 36 moves relative to the gantry 34 and/or relative to the subject 14, the size, shape, and position of the selected opening 1720 relative to the stage 1620 may change. The instructions stored in the memory 33b may be used to move the selected opening 1720 relative to the stage 1620 as the source unit 36 moves relative to the gantry 34. Moreover, the controller 32 may receive feedback from the respective read heads 1702a-1702d to determine the position of the leaves 1630-1636 to determine further and/or appropriate movements of the motors 1650-1656 to position the respective leaves 1630-1636 to form the selected opening 1720 of a selected size and/or position.

The leaves 1630-1636, as illustrated in FIG. 11, are positioned to move from one side of the stage aperture 1624 and an edge of the stage 1620. Each of the motors 1650-1656 have portions (e.g. motor coils) fixed on a single side of the stage aperture and move the respective leaf carriers 1670a-1670d from the one side towards and over the stage aperture. Generally, as illustrated in FIG. 11, the leaves 1630-1636 may not extend across the stage 1620 from one side to another. It is understood, however, that at least one of the leaves 1630-1636 may extend across the stage 1620.

Figure 12:
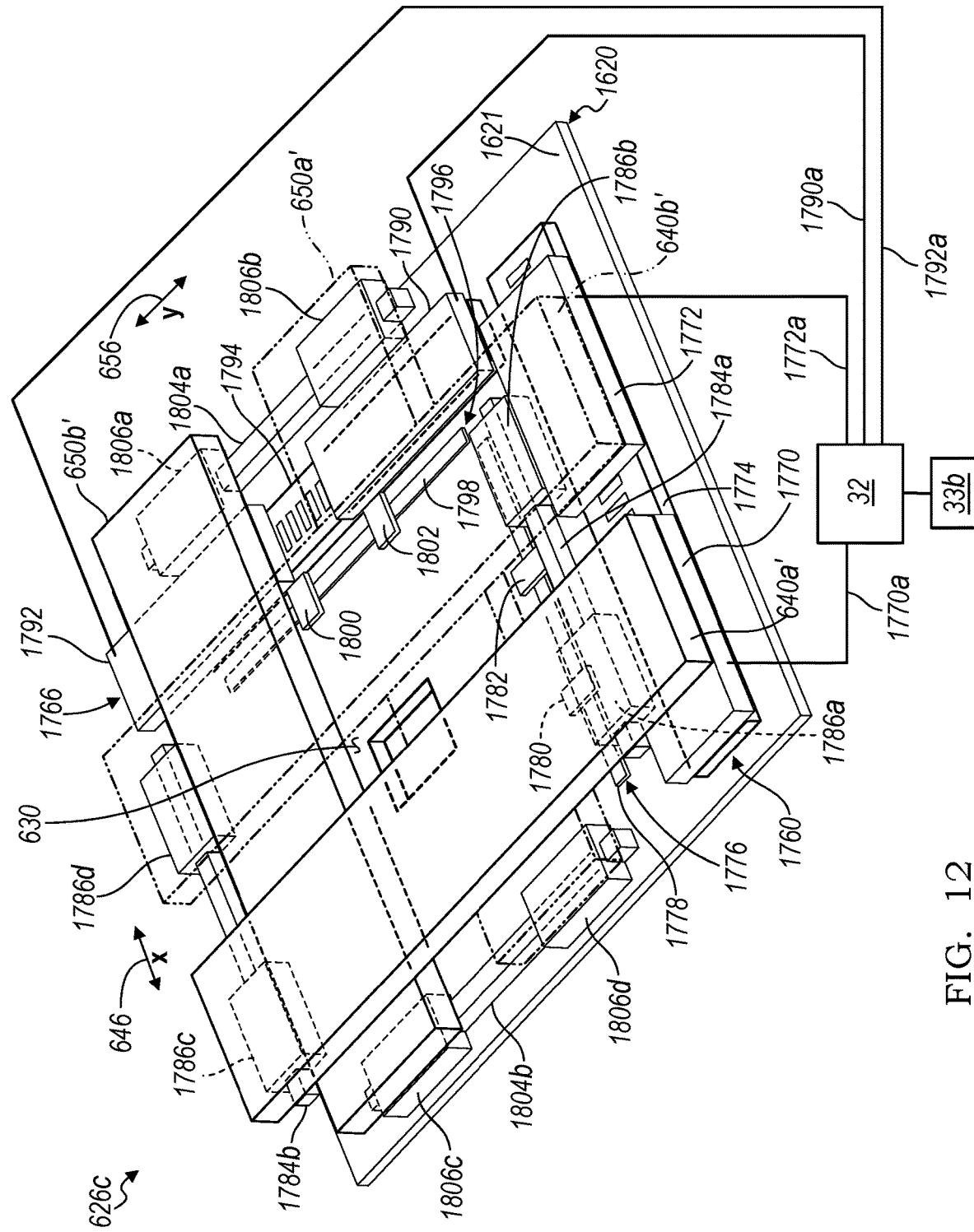
FIG. 12 is a perspective view of a X and Y axis selection assembly for the multiple-axis collimator assembly, according to various embodiments.

With reference to FIG. 12, an ASA 626c is illustrated. The ASA 626c may include components of both of the ASA 626a and the ASA 626b, as discussed above and illustrated in FIGS. 9-11. The ASA 626c includes the leaves 640' and 650', similar to the ASA 626a. In the ASA 626c, however, the leaves 640', 650' are moved with linear motors (as discussed herein) similar to the linear motors discussed in the ASA 626b. Rather than providing the drive mechanisms 690 and 750, as discussed above in the ASA 626a, linear motors are provided to drive the leaves 640', 650'.

The leaves 640', 650' may be on leaf carriers 674, 780 as discussed above, or may be directly connected to respective pairs of parallel rails. Regardless, each one of the leaves may be interconnected with a separate linear motor to individually move each of the leaves. Each leaf may be interconnected with a single linear motor drive mechanism and the respective pairs of rails to allow for non-binding and smooth movement of the leaves.

As noted above, the ASA 626c may include portions similar or identical to the ASA 626a. With reference to FIG. 12, the ASA 626c may be mounted to the stage 1620. The ASA 626c may include the leaves 640'a and 640'b that may move generally in the direction of double headed arrow 646 along the X axis. As illustrated in FIG. 12, the leaves 640', at only one end or at both ends, may be directly connected to a linear motor drive mechanism 1760. It is understood, however, that the leaves 640' may be connected to leaf carriers (not illustrated in FIG. 12) similar to leaf carriers 674 discussed above. The ASA 626c further includes two leaves 650'a and 650'b. The leaves 650' may be directly connected to a second linear drive mechanism 1766, at only one or at both ends, to move the leaves 650 generally in the direction of double headed arrow 656 in the Y axis. It is understood, however, that the leaves 650' may also be connected to leaf carriers such, as the carriers 780, as discussed above for the ASA 626a. As illustrated in FIG. 12, and further discussed further herein, however, it is understood that leaf carriers are not required and that the leaves 640', 650' may be directly connected to the linear drive mechanisms 1760 and 1766.

As illustrated in FIG. 12, the leaves 640' and 650' may be moved relative to the stage 1620 to form the selected opening 630. The leaves 640', 650' are connected with the respective drive mechanisms 1760, 1766 at only one end or a single end of the respective leaves 640', 650'. In various embodiments, drive mechanisms may be provided at both ends, if selected. Various bearing and/or rail systems assist in ensuring smoothing and binding free movement of the leaves 640', 650', particularly with the linear motor drive mechanisms connected to only one end of the leaves 640', 650'. Similarly, the drive mechanisms 1760, 1766 may be connected to only one end of the leaves 640', 650', similar to the connection of the ASA 626a.

The first leaf 640'a is connected to a first moving coil 1770. The moving coil may be fixed to the leaf 640'a in any appropriate manner such as with an adhesive, welding, or fastener (e.g., rivet, screw, or the like) or other appropriate connection mechanism. The second leaf 640'b is connected to a second moving coil 1772 in a manner similar to the moving coil 1770 connected to the leaf 640'a. Both of the moving coils 1770, 1772 move along a common magnet 1774. The common magnet 1774 forms a common portion for the drive mechanism 1760 and forms a linear motor with respect to both of the moving coils 1770, 1772. The linear motor of the drive mechanism 1760 may operate in a manner similar to that of the linear motors (e.g. 1650, 1652, 1654, 1656 as discussed above. The moving coils 1770, 1772 of the linear motor drive mechanism 1760 may move each of the respective leaves 640'a and 640'b in the direction of the double headed arrow 646. The respective moving coils 1770 and 1772 are connected with the controller 32 with an appropriate communication system 1770a and 1772a, respectively. The controller 32 may operate the linear motor drive mechanism 1760 to move the leaves 640' in the X axis to position and size the selected opening 630 in the X axis. The controller 32 may be manually operated or may execute instructions using the processor 33a based on instructions saved and recalled from the memory 33b.

The position of the leaves 640'a and 640'b may be determined with a position sensor 1776, similar to the positions sensors 290 discussed above. The position sensor 1776 includes a linear or elongated sensor 1778 and a first read head 1780 fixedly connected to the moving coil 1770 and/or the leaf 640'a to move relative to the sensor 1778. A second read head 1782 is fixedly connected to the second moving coil 1772 and/or the second leaf 640'b to move relative to the sensor 1778. As discussed above, the respective read heads 1780, 1782 may be connected via the respective communication systems 1770a and 1772a with the controller 32 such that a position signal may be transmitted to the controller 32 and the controller 32 may be operated to control the drive mechanism 1760 based upon the position signal from the position sensor 1776.

Further, the leaves 640' may be interconnected with bearings or a pair of parallel rails 1784a and 1784b. The leaves 640'a, 640'b may be directly connected to the rails 1784 and/or interconnected with respective cars or bearing trucks 1786a, 1786b, 1786c, 1786d. Therefore, the leaves 640' may move in a path defined by the rails 1784 along the X-axis. Further, the interconnection of the leaves 640' with the rails 1784 allows for substantially smooth and non-binding motion in the X-axis.

The leaves 640', configured to move in the X-axis, may be offset a distance from a surface 1621 of the stage 1620 greater than a distance of the leaves 650'. As discussed further herein, the leaves 650' may move in the Y-axis which may be substantially perpendicular to the X axis. Therefore, to have non-interfering movement of the leaves 640' in the X axis and the leaves 650' in the Y axis, the leaves may be positioned in different planes so as to not contact one another to allow for ease of movement of the respective leaves.

The leaves 650' are connected with the drive mechanism 1766 at one end of the leaves 650'. Similar to the leaves 640', the leaf 650'a is fixedly connected to a third moving coil 1790 and the fourth leaf 650'b is fixedly connected to a fourth moving coil 1792. The third and fourth moving coils 1790, 1792 move along a single and common magnet 1794 to form the linear motor drive mechanism 1766. Again, each of the moving coils 1790, 1792 are connected with the controller 32 with respective and appropriate communication systems 1792a and 1790a. Again, it is understood that the communication systems 1770a, 1772a, 1790a, and 1792a may be wired communication systems, wireless communication systems, physical media transmission systems, or other appropriate communication systems. The controller 32 may operate the drive mechanism 1766 to move the leaves 650' in a manner similar to that described above to operate a linear motor.

Further, the controller 32 may receive position signals from a position sensor 1796 associated with the drive system 1766. The position sensor 1796 may include a single scale sensor 1798. A third read head 1800 may be fixed to the moving coil 1790 and/or the third leaf 650'a. A fourth read head 1802 may be fixed to the fourth moving coil 1792 and/or the fourth leaf 650'b. Both of the read heads 1800, 1802 may move along the sensor 1798 to provide a common reference position sense and position signal for the drive system 1766. The position signal may be transmitted to the controller 32 with the respective communication systems 1790a and 1792a. The controller 32, therefore, may know or determine the position of the leaves 650'a and 650'b with the position signal from the position sensor 1796.

The drive mechanism 1766 is connected to one end of the leaves 650'. The leaves 650', however, may be interconnected with a bearing system including a third rail 1804a and a fourth rail 1804b. The rails 1804a, 1804b may form a second pair of rails or bearings that is substantially perpendicular to the bearing rails 1784a, 1784b. The leaves 650' may directly engage the rails 1804 and/or may be connected with cars or moving bearings or trucks 1806a, 1806b, 1806, and 1806d. Regardless, the rails 1804 allow for substantially smooth and non-binding movement of the leaves 650'.

The ASA 626c, therefore, may include leaves substantially similar or identical leaves to the 640, 650 of the ASA 626a and drive mechanisms similar to the drive mechanisms of the ASA 626b. The leaves 640', 650' of the ASA 626c may be moved to form the selected opening 630 in a manner similar to the leaves 640, 650 of the ASA 626a with the alternative motors or drive mechanisms 1760 and 1766. The leaves 640', 650' may, as illustrated in FIG. 12, extend from one side of the stage 1620 to a second side of the stage 1620 and may cross the stage aperture 1624. For example, the rails of the rail pairs 1784, 1804 are spaced across the stage aperture 1624 from one another. Thus, the leaves 640', 650' may span or cross the stage 1620. Further, the leaves 640', 650' may be interconnected with moving magnets rather than moving coils, as discussed above. Accordingly, it is understood, that the ASA 626c may be controlled with instructions to form the selected opening 630 similar to the manner of the ASA 626a as discussed above. It is further understood, however, that the individual connections of the coils 1770, 1772 to the leaves 640', 650' may allow for independent movement (e.g. amount and/or direction) of each of the leaves 640'*a*, 640'*b*, 650'*a*, and 650'*b* relative to one another and the stage 1620.

The collimator 198, as illustrated in FIG. 9 may also include filters in addition to the high speed filter 200, according to various embodiments including the high speed filter 200c, as illustrated in FIG. 9. Additional filters may include filtering elements or portions for various features such as tailoring the beam spectrum to optimize imaging performance when acquiring the image data. The filters may be provided in a multiple element or position filter assembly 2000. The filter assembly 2000 may include a plurality of filter positions or locations 2010, including individual positions 2010*a*, 2010*b*, 2010*c*, 2010*d*, 2010*e*, 2010*f*, 2010*g*, and 2010*h*. The filter locations 2010 may be formed as passages or openings in a filter carrier or plate 2014. At each of the filter positions 2010, a selected filter material may be included. The filter material may be placed in a void or opening formed in the filter carrier 2014. The filter material may be opaque or transparent to various wavelengths or energies. For example, the filter position 2010*a* may include a filter material such as copper, tin, silver, aluminum, alloys thereof, layered materials, or other appropriate material with a selected Z reference value that limits or selected a type or energy level of x-rays for passing through the exposure opening 600 of the collimator 198. Further, one or more of the filter positions 2010 may not include any filter material, thus providing a void, to form an unfiltered passage through the filter carrier 2014 for x-rays or other emissions. Certain filter materials or materials may be provided that do not substantially interact with x-rays so that the filter position acts as a void even if a material is within the path of the x-rays.

The filter plate 2014 may be formed as a substantially circular plate member having exterior perimeter teeth 2020. The teeth 2020 allow the filter carrier 2014 to be rotated around a central axis 2022 on an axle or spindle 2024 to position one of the filter positions 2010 relative to the exposure opening 600. The external teeth 2020 may be engaged by a spindle gear 2030 having external teeth that is driven by a motor assembly 2032. The motor assembly 2032 may be controlled by the controller 32 through a communication system 2034. The communication system may be any appropriate communication system, such as a wired, wireless, or other appropriate communication system. The motor assembly 2032 may include any appropriate type of motor such as a servo motor or stepper motor. The motor assembly 2032 may drive the external gear 2030 to rotate the filter carrier 2014 according to a selected plan or instructions, such as instructions that may be stored on the memory 33*b*.

The filter assembly 2000 may further include a position sensor assembly 2040 that may communicate with a controller 32 through a communication line 2042. The position sensor 2040 may include a spindle gear 2044 that is engaged on the exterior teeth 2020 of the filter carrier 2014. As the filter carrier 2014 rotates, the spindle gear 2044 may also rotate and the sensor 2040 may determine a relative or absolute position of the filter carrier 2014 based upon movement of the spindle gear 2044.

The position sensor 2040 may include an optical or mechanical encoder, such as the US Digital® S4T optical shaft encoder. Based upon the position sensor 2040, the motor 2032 may be operated to position a selected one of the filter elements in a selected one of the filter positions 1020*a-h* relative to the exposure opening 600. The filter carrier 2014 may spin or rotate on the axis 2022 on the axle 2024 that is selectively fixed to the frame 660. The frame 660 that may hold the ASA 626*a* may be fixed relative to the exposure opening 600. It is understood, however, that the axle 2024 may be fixed to any appropriate portion of the collimator 198, including the housing 608. Therefore, the position of the filter carrier 2014 may be rotated relative to the exposure opening 600 by operating the motor 2032. Similarly, the high speed filter 200*c* may be mounted on the frame 660.

With continued reference to FIG. 9 and additional reference to FIG. 13, a multiple element or position filter assembly 2100 is illustrated. The filter assembly 2100 may include a filter carrier 2110. The filter carrier 2110 may include the plurality of filter positions 2010*a*-2010*h*, similar to the filter positions discussed above of the filter assembly 2000. Again, the filter carrier 2110 may be rotated around the axis 2022 on an axle 2130 to position one of the filter positions 2010*a-h* relative to the exposure opening 600, to position the filter position 2010 relative to the exposure opening 600.

The filter assembly 2100, however, may be driven by a drive assembly similar to the drive assembly of the high speed filter 200*c*, as discussed above and illustrated in FIG. 5 and FIG. 6. The drive assembly for the filter assembly 2100, therefore, may include the carry gear 360 (not illustrated in FIG. 13) which holds or carries the filter carrier 2110, as discussed above. The carrier gear 360 may be driven by the belt 364 that is driven by the drive gear 366 on the shaft 370. The shaft 370 may be driven by the motor assembly 374. As discussed above, the motor assembly 374 may include a motor within a housing 376 that may be controlled by the controller 32 with the communication or control line 380. The motor assembly 374 may be controlled to position a selected one of the filter positions 2010 relative to the opening 600 in a manner similar to that discussed above. The different positions 2010 may be identified with various sensors, such as index sensors and the like to determine the position of the filter plate 2110. The filter assembly 2000, however, may be operated in a non-continuous motion operation, therefore absolute position sensors may be used to determine which of the filter positions 2010*a-h* are aligned with the exposure opening 600.

The plurality of filter portions 2010*a-h* of the filter assembly 2000 and the filter assembly 2100 generally allows one of the filter positions 2010*a-h* to be positioned relative to the exposure opening 600 for a selected period of time. Therefore, the filter plate or carrier 2014 or 2110 generally may not rotate continuously during an imaging procedure. Accordingly, the motor assembly and sensors may be selected based upon the reduced amount of motion and may include absolute position sensors to determine a position of the filter carrier, including the filter positions 2010 relative to the opening 600.

With reference to FIG. 14, a filter assembly 2200 is illustrated. The filter assembly 2200 is illustrated positioned relative to the stage 1620 of the ASA 626*b* illustrated in FIG.

11. It is understood, however, that the filter assembly 2200 may be positioned relative to any appropriate portion of the collimator 198. The filter assembly 2200 may include a grid or patterned filter carrier 2210 that includes a plurality of filter positions or openings 2220*a*-2220*i*. The filter carrier may move in a plane and generally in two axes, e.g. X-axis and Y-axis.

Each of the filter positions 2220 may include a different filter material and/or be open to not filter any transmission through the exposure opening 1624. The filter carrier 2210 may be moved relative to the exposure opening 1624 and/or the opening 600 of the collimator 198 by movement along parallel rails. A first set of parallel rails includes a first rail 2230*a* and 2230*b*. The first set of parallel rails 2230 may be fixed to the stage 1620. A number of cars, including four cars 2232*a*-2232*d* may move along the rails 2230 generally in the direction of the double-headed arrow 2236.

Mounted to the first set of cars 2232 may be a plurality of additional cars 2240*a*-2240*d* as the first set of cars 2230 move in the direction of double-headed arrow 2236, they move the second set of cars 2240 in the same direction. Movable relative to the second set of cars 2240 may be a second set of rails including a third rail 2250*a* and fourth rail 2250*b*. The second set of rails 2250 may generally move in a direction of double-headed arrow 2254. The filter carrier 2210 may be fixed to the second set of rails 2250 in any appropriate manner, such as with welding, adhesives, or fasteners.

As the second set of rails 2250 moves in the direction of double-headed arrow 2254, the filter carrier 2210 also moves in the direction of the double-headed arrow 2254. Further, because the rail members 2250 are interconnected with the first set of cars 2232, the frame carrier 2210 also moves in the direction of double-headed arrow 2236 in a selected manner. Therefore, the filter carrier 2210 may be moved relative to the exposure opening 1624 in the stage 1620 and/or the exposure opening 600 in the direction of either double-headed arrow 2236 or 2254, such as x and y directions.

Movement of the cars 2232 or the rails 2250, relative to the cars 2240, may be formed in any appropriate manner. For example, as discussed above, lead screws driven by selected motors (e.g., servo motors or stepper motors), linear motors, or other appropriate motor drive mechanisms may be used to move the respective cars 2232 and/or the rails 2250. In this way the filter carrier 2210 may be moved relative to the exposure opening 1624.

According to various embodiments, the frame carrier 2210 may include only a single row of filter positions, rather than a grid. In a single row, the frame carrier need only move in a single axis, such as only translate along the X-axis. In such a configuration, the frame carrier may resemble a ladder where a filter position is between each rung of the ladder. The ladder filter carrier may also reduce the number of rails and/or cars riding on rails needed to move the ladder. For example, the ladder may be moved on a single pair of parallel rails in the X-axis. The ladder frame carrier may be moved in two directions, however, along the X-axis. The movement of the ladder filter carrier may be powered by any selected appropriate motor, such as linear motors as discussed above. The linear motor may be positioned to move the ladder filter carrier relative to the exposure opening 600. Further, the ladder filter carrier may be moved based on instructions or control from the controller 32.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. An assembly for an imaging system, comprising:
   a stage having a surface and a stage aperture through the stage;
   a first track pair fixed relative to the surface extending along a first axis;
   a second track pair fixed relative to the surface extending along a second axis, wherein the second axis is substantially perpendicular to the first axis;
   a first leaf and a second leaf configured to move opposed to one another;
   a third leaf and a fourth leaf configured to move opposed to one another;
   a first linear motor drive mechanism attached to the first leaf and to the second leaf to move the first leaf and the second leaf along the first axis; and
   a second linear motor drive mechanism attached to the third leaf and to the fourth leaf to move the third leaf and the fourth leaf along the second axis; and
   wherein the first leaf and the second leaf are moveably connected to the first track pair;
   wherein the third leaf and the fourth leaf are movably connected to the second track pair.

2. The assembly of claim 1, wherein the first linear motor drive mechanism includes a first moveable coil fixed to the first leaf and a second moveable coil fixed to the second leaf;
   wherein the second linear motor drive mechanism includes a third moveable coil fixed to the third leaf and a fourth moveable coil fixed to the fourth leaf.

3. The assembly of claim 2, wherein the first linear motor drive mechanism includes a first common magnet relative to which each of the first moveable coil and the second moveable coil move;
   wherein the second linear motor drive mechanism includes a second common magnet relative to which each of the third moveable coil and the fourth moveable coil move.

4. The assembly of claim 2, wherein the first moveable coil is attached to only one end of the first leaf, the second moveable coil is attached to only one end of the second leaf, the third moveable coil is attached to only one end of the third leaf, and the fourth moveable coil is attached to only one end of the fourth leaf.

5. The assembly of claim 1, further comprising:
   a first position sensor interconnected with the first leaf;
   a second position sensor interconnected with the second leaf;
   a third position sensor interconnected with the third leaf;
   a fourth position sensor interconnected with the fourth leaf;
   a controller configured to receive a position signal from each of the first position sensor, second position sensor, third position sensor, and fourth position sensor;
   a communication system connecting the controller and each of the first linear motor drive mechanism and the second linear motor drive mechanism;
   wherein the controller is configured to operate each of the first linear motor drive mechanism and the second linear motor drive mechanism to move the respective first leaf, second leaf, third leaf, and fourth leaf based at least one the position signal from the respective first position sensor, second position sensor, third position sensor, and fourth position sensor.

6. The assembly of claim 1, wherein the first drive mechanism includes a first linear motor having a first motor coil and a first motor magnet and a second linear motor having a second motor coil and a second motor magnet;
wherein the second linear motor drive mechanism includes a third linear motor having a third motor coil and a third motor magnet and a fourth linear motor having a fourth motor coil and a fourth motor magnet.

7. The assembly of claim 6, wherein each of the first leaf, the second leaf, the third leaf, and the fourth leaf are moveably connected to one of the first linear motor, the second linear motor, the third linear motor, and the fourth linear motor.

8. The assembly of claim 1, wherein each of the first leaf and the second leaf extend a first distance across the stage and are configured to cross the stage aperture;
wherein each of the third leaf and the fourth leaf extend a second distance across the stage and are configured to cross the stage aperture.

9. An assembly for an imaging system, comprising:
a stage having a surface and a stage aperture through the stage;
a first leaf and a second leaf configured to move opposed to one another and move in a first plane relative to the surface of the stage;
a third leaf and a fourth leaf configured to move opposed to one another in a second plane relative to the surface of the stage;
a first linear motor interconnected to the first leaf to move the first leaf in a first axis in the first plane;
a second linear motor interconnected to the second leaf to move the second leaf along the first axis in the first plane;
a third linear motor interconnected to the third leaf to move the third leaf along a second axis in the second plane; and
a fourth linear motor interconnected to the fourth leaf to move the fourth leaf along the second axis in the second plane;
wherein the first leaf and the second leaf are moveably connected to move toward and away from one another;
wherein the third leaf and the fourth leaf are movably connected to move toward and away from one another.

10. The assembly of claim 9, wherein the first linear motor a includes a first moveable magnet fixed relative to the first leaf, the second linear motor includes a second moveable magnet fixed relative to the second leaf, the third linear motor includes a third moveable magnet fixed relative to the third leaf, and the fourth linear motor includes a fourth moveable magnet fixed relative to the fourth leaf.

11. The assembly of claim 10, further comprising:
a first leaf carrier having a first leaf holding region, wherein the first moveable magnet is attached to the first leaf carrier;
a second leaf carrier having a second leaf holding region, wherein the second moveable magnet is attached to the second leaf carrier;
a third leaf carrier having a third leaf holding region, wherein the third moveable magnet is attached to the third leaf carrier; and
a fourth leaf carrier having a fourth leaf holding region, wherein the fourth moveable magnet is attached to the fourth leaf carrier.

12. The assembly of claim 11, wherein each of the first leaf carrier, the second leaf carrier, the third leaf carrier, and the fourth leaf carrier are configured to move the respective first leaf, second leaf, third leaf, and fourth leaf relative to the stage aperture from a single side of the stage aperture.

13. The assembly of claim 9, wherein each of the first linear motor, the second linear motor, the third linear motor, and the fourth linear motor are mounted separately on the surface of the stage.

14. The assembly of claim 9, further comprising:
a first position sensor interconnected with the first leaf;
a second position sensor interconnected with the second leaf;
a third position sensor interconnected with the third leaf;
a fourth position sensor interconnected with the fourth leaf;
a controller configured to receive a position signal from each of the first position sensor, second position sensor, third position sensor, and fourth position sensor;
a communication system connecting the controller and each of the first linear motor, the second linear motor, the third linear motor, and the fourth linear motor;
wherein the controller is configured to operate each of the first linear motor, the second linear motor, the third linear motor, and the fourth linear motor to move the respective first leaf, second leaf, third leaf, and fourth leaf based at least on the position signal from the respective first position sensor, second position sensor, third position sensor, and fourth position sensor.

15. An assembly for an imaging system, comprising:
a stage having a surface and a stage aperture through the stage;
a first leaf and a second leaf configured to move opposed to one another and move in a first plane relative to the surface of the stage;
a third leaf and a fourth leaf configured to move opposed to one another in a second plane relative to the surface of the stage;
a first linear motor interconnected to the first leaf to move the first leaf in a first axis in the first plane; and
a second linear motor interconnected to the second leaf to move the second leaf along the first axis in the first plane;
wherein the first leaf and the second leaf are moveably connected to move toward and away from one another;
wherein the third leaf and the fourth leaf are movably connected to move toward and away from one another.

16. The assembly of claim 15, wherein the first linear motor includes a first moveable magnet fixed relative to the first leaf, and the second linear motor includes a second moveable magnet fixed relative to the second leaf.

17. The assembly of claim 16, further comprising:
a first leaf carrier having a first leaf holding region, wherein the first moveable magnet is attached to the first leaf carrier; and
a second leaf carrier having a second leaf holding region, wherein the second moveable magnet is attached to the second leaf carrier.

18. The assembly of claim 17, wherein each of the first leaf carrier and the second leaf carrier are configured to move the respective first leaf and second leaf relative to the stage aperture from a single side of the stage aperture.

19. The assembly of claim 15, wherein each of the first linear motor and the second linear motor are mounted separately on the surface of the stage.

20. The assembly of claim 15, further comprising:
a first position sensor interconnected with the first leaf;

a second position sensor interconnected with the second leaf;

a controller configured to receive a position signal from each of the first position sensor and the second position sensor;

a communication system connecting the controller and each of the first linear motor and the second linear motor;

wherein the controller is configured to operate each of the first linear motor and the second linear motor to move the respective first leaf and second leaf based at least on the position signal from the respective first position sensor and second position sensor.

21. The assembly of claim 15, further comprising:

a third linear motor interconnected to the third leaf to move the third leaf along a second axis in the second plane;

a fourth linear motor interconnected to the fourth leaf to move the fourth leaf along the second axis in the second plane;

the third linear motor includes a third moveable magnet fixed relative to the third leaf, and the fourth linear motor includes a fourth moveable magnet fixed relative to the fourth leaf;

a third leaf carrier having a third leaf holding region, wherein the third moveable magnet is attached to the third leaf carrier; and a fourth leaf carrier having a fourth leaf holding region, wherein the fourth moveable magnet is attached to the fourth leaf carrier.

* * * * *